(12) United States Patent
Eugen-Olsen

(10) Patent No.: US 7,399,602 B2
(45) Date of Patent: Jul. 15, 2008

(54) METHOD OF PROGNOSTICATING RESPIRATORY BACTERIAL INFECTION USING UROKINSE RECEPTOR MEASUREMENT

(75) Inventor: Jesper Eugen-Olsen, Hellerup (DK)

(73) Assignee: ViroGates A/S, Birkerod (DK)

( * ) Notice: Subject to any disclaimer, the term of this patent is extended or adjusted under 35 U.S.C. 154(b) by 432 days.

(21) Appl. No.: 10/478,331

(22) PCT Filed: May 21, 2002

(86) PCT No.: PCT/DK02/00341

§ 371 (c)(1),
(2), (4) Date: Mar. 11, 2004

(87) PCT Pub. No.: WO02/095411

PCT Pub. Date: Nov. 28, 2002

(65) Prior Publication Data

US 2005/0100961 A1    May 12, 2005

(30) Foreign Application Priority Data

May 18, 2001 (DK) ............................... 2001 00799

(51) Int. Cl.
*G01N 33/569* (2006.01)
*G01N 33/566* (2006.01)
(52) U.S. Cl. ..................... 435/7.34; 435/4; 435/7.2; 435/7.32
(58) Field of Classification Search ................... None
See application file for complete search history.

(56) References Cited

U.S. PATENT DOCUMENTS 4,845,026 A  7/1989 Kung et al.
5,459,078 A  10/1995 Kline et al.

FOREIGN PATENT DOCUMENTS

| CA | 2318740 | 7/1999 |
| CA | 2384295 | 11/2000 |
| DE | 19840671 | 3/2000 |
| WO | WO-01/38871 A1 | 5/2001 |

OTHER PUBLICATIONS

Nykjaer, Anders, et al., "Urokinase Receptor, An Activation Antigen in Human T Lymphocytes", Journal of Immunology, 1994, vol. 152, pp. 505-516.
Speth, Cornelia, et al., "Urokinase Plasminogen Activator Receptor (uPAR; CD87) Expression on Monocytic Cells and T Cells is Modulated by HIV-1 Infection," Immunobiology, 1998, vol. 199, pp. 152-162.
Mustjoki, Satu, et al., "Soluble Urokinase Receptor Levels Correlate with Number of Circulating Tumor Cells in Acute Myeloid Leukemia and Decrease Rapidity during Chemotherapy", Cancer Research, Dec. 15, 2000, vol. 60, pp. 7126-7132.
Rha, Sun Young, et al., "Correlation of tissue and blood plasminogen activation system in breast cancer," Cancer Letters, 2000, vol. 150, pp. 137-145.
Hengge, Ulrich R., et al., "Randomized, controlled phase II trial of subcutaneous interleukin-2 in combincation with highly active antiretroviral therapy (HAART) in HIV patients", AIDS, 1998, vol. 12, No. 17, pp. F225-F234.
Stephens, Ross W., et al., "ELISA determination of soluble urokinase receptor in blood from healthy donors and cancer patients", Clinical Chemistry, 1997, vol. 43, No. 10, pp. 1868-1876.
Apr. 23, 2001 International Search Report issued during prosecution of PCT/DK00/00651.
Dekkers, Pascale E.P., et al., "Upregulation of Monocyte Urokinase plasminogen Activator Receptor during Human Endotoxemia", Infection and Immunity, vol. 68, No. 4, Apr. 2000, pp. 2156-2160.
Coleman, James L., et al. "*Borrelia burgdorferi* and Other Bacterial Products Induce Expression and Release of the Urokinase Receptor (CD87)1", The Journal of Immunology, vol. 166, 2001, pp. 473-480.
Florquin, et al., "Release of urokinase plasminogen activator receptor during urosepsis and endotoxemia", Kidney International, vol. 59, 2001, pp. 2054-2061.
Fauser, Susanne, et al., "Lesion associated expression of urokinase-type plasminogen activator receptor (uPAR, CD87) in human cerebral malaria", Journal of Neuroimmunology, vol. 111, 2000, pp. 234-240.
Heegaard, C.W., et al., "Plasminogen Activators in Bovine Milk During Mastitis, an Inflammatory Disease", Fibrinolysis, vol. 8, 1994, pp. 22-30.
Todd, Robert F., et al., "Bacterial lipopolysaccharide, phorbol myristate acetate, and muramyl dipeptide stimulate the expression of a human monocyte surface antigen", The Journal of Immunology, vol. 135, No. 6, Dec. 1985, pp. 3869-3877.
Eugene-Olsen, J., et al., "The serum level of soluble urokinase receptor is elevated in tuberculosis patients and predicts mortality during treatment: a community study from Guinea-Bissau" Int. K. Tuberc. Lung Dis., vol. 6, No. 8, 2002, pp. 686-692.
Juffermans, Nicole P., et al., "Concurrent Upregulation of Urokinase Plasminogen Activator Receptor and CD11b during Tuberculosis and Experimental Endotoxemia", Infection and Immunity, vol. 69, No. 8, 2001, pp. 5182-5185.
Garcia-Monco, Juan Carlos, et al., "Soluble urokinase receptor (uPAR, CD 87) is present in serum and cerebrospinal fluid in patients with neurologic diseases", Journal of Neuroimmunology, vol. 129, 2002, pp. 216-223.
Indian Patent Office First Examination Report.

*Primary Examiner*—Michael Pak
(74) *Attorney, Agent, or Firm*—Darby & Darby P.C.

(57) ABSTRACT

Method of diagnosing and/or prognosticating HIV infection in a subject comprising the steps of: (a) performing in vitro a measurement of the level of a marker in the form of (i) urokinase plasminogen activator receptor (uPAR), (ii) soluble urokinase plasminogen activator receptor (suPAR), (iii) urokinase-type plasminogen activator (uPA), (iv) one or more degradation products of (i), (ii) or (iii), and/or (v) an mRNA for (i), (ii) or (iii), in a biological fluid sample from a subject, and (b) using the measurement value obtained to evaluate the state of the subject.

17 Claims, 12 Drawing Sheets

METHOD OF PROGNOSTICATING RESPIRATORY BACTERIAL INFECTION USING UROKINSE RECEPTOR MEASUREMENT

TECHNICAL FIELD OF THE INVENTION

The present invention concerns the diagnosis and/or prognosis of major respiratory bacterial pathogens. In particular it concerns *Streptococcus pneumoniae* and *Mycobacterium tuberculosis*. More particular it concerns the measurements of the concentration of soluble urokinase plasminogen activator receptor (suPAR) in human biological fluids (sputum, cystic fluid, ascites, serum, plasma, urine) as a tool of diagnosing respiratory bacterial infection as well as the prognosis of disease progression.

BACKGROUND OF THE INVENTION

The cellular receptor for urokinase (uPAR, CD87) plays multiple functions in cell migration, cell adhesion, pericellular proteolysis and tissue remodeling. uPAR is expressed by most leukocytes including monocytes, macrophages, neutrophils and platelets. uPAR is an activation antigen in monocytes and T cells and T-cells from HIV-1 infected individuals express elevated levels of uPAR[1], 1994. HIV-1 infection of leukocytes in vitro causes up-regulation of uPAR cell surface expression in a process which appear to be coordinated temporally with the onset of viral replication[2].

uPAR may be shed from the cell surface generating a soluble form of the receptor (suPAR) lacking the GPI-anchor. The shedding mechanism is poorly understood but may occur by GPI-specific phospholipase D catalyzed hydrolytic cleavage of the GPI-anchor). Soluble forms of uPAR (suPAR) has been identified in cell culture supernatants and in diverse biological fluids such as tumor ascites, cystic fluid, serum, plasma and recently also in urine [3].

Serum, plasma and urine levels of suPAR are elevated in patients suffering from different types of cancer[4], the paroxysmal nocturnal hemoglobinuria syndrome (PNH) syndrome[5], and in rheumatoid arthritis patients[6]. The plasma level of suPAR is furthermore a prognostic marker for overall survival in patients suffering from HIV-1 infection[7].

The cellular origin of circulating suPAR is not known. Many, if not all, cells which express uPAR also shed soluble forms of the receptor when cultured in vitro. The source of excess serum suPAR in cancer patients has been suggested to derive from the cancer cells and/or tumor-infiltrating macrophages as these cells often express high levels of uPAR and experiments using xenografted mice carrying human tumors have indeed demonstrated that the tumor tissue does release suPAR to the circulation and urine[8].

SUMMARY OF THE INVENTION

The technical problem addressed by the present invention is to provide a novel marker for diagnosing and prognosticating major respiratory bacterial pathogens, in particular *Streptococcus pneumoniae* and *Mycobacterium tuberculosis*. A further technical problem addressed by the present invention is to provide a marker of the said type, which is simple and affordable to measure.

The present invention has provided a solution to the above technical problems, the invention being directed to a method of diagnosing or prognosticating major respiratory bacterial pathogens, such as *Streptococcus pneumoniae* and *Mycobacterium tuberculosis* in a subject comprising the steps of (a) performing in vitro a measurement of the level of one or more markers in the form of (i) urokinase plasminogen activator receptor (uPAR), (ii) soluble urokinase plasminogen activator receptor (suPAR), and/or (iii) one or more degradation products of (i) or (ii), in a biological fluid sample from a subject, and (b) using the measurement value obtained to evaluate the state of the subject.

The invention is based on the surprising discovery that soluble uPAR (suPAR) is present in elevated levels in serum, plasma and urine of patients with two major respiratory bacterial pathogens, *Streptococcus pneumoniae* and *Mycobacterium tuberculosis*, and that the level of suPAR is useful as a diagnostic marker. Also, the level of suPAR in individuals with two major respiratory bacterial pathogens, *Streptococcus pneumoniae* and *Mycobacterium tuberculosis* is prognostic for the development of the disease and death. The suPAR level is a novel and highly diagnostic and prognostic factor, even in the context of other known prognostic factors related to *Streptococcus pneumoniae* or *Mycobacterium tuberculosis* infection of the lung.

Furthermore, the present invention is based on the recognition that the amount of suPAR is correlated to the amount of uPAR and that therefore the amounts of uPAR is equally suitable as diagnostic and prognostic indicators of tuberculosis infection.

A further advantage of the invention is that measurement of suPAR can be performed using e.g. a simple ELISA technique or even a stick and may therefore provide a very inexpensive, simple and quick supplement to the currently used prognostic tools for persons infected with tuberculosis. Thus, in developing countries without the financial possibility to carry out the costly assays used in the western world, suPAR levels could be used 1) to determine tuberculosis status (diagnosis), 2) to select patients for treatment (prognosis), and 3) to monitor the progress of treatment.

Furthermore, the present invention involves the advantage that while suPAR levels can be measured very simply, using e.g. a urine sample or sputum sample, which is easy to obtain, conventional diagnostic and prognostic tests for e.g. tuberculosis are uncertain, complex and involve e.g. growth in culture of sputum, clinical testing and chest x-ray.

The invention further relates to a method of evaluating the progression of the state of a subject suffering from a major respiratory bacterial pathogen, such as tuberculosis or *Streptococcus pneumoniae* comprising the steps of (a) performing in vitro a measurement of the level of one or more markers in the form of (i) urokinase plasminogen activator receptor (uPAR), (ii) soluble urokinase plasminogen activator receptor (suPAR), and/or (iii) one or more degradation products of (i) or (ii), in each of a number of biological fluid samples from a subject, wherein the samples are obtained at different points in time, and (b) using the measurement values obtained to evaluate the progression of the state of the subject.

This method may be used to continuously monitor the state e.g. the treatment efficacy of the patient.

Finally, the present invention relates to an ELISA-kit and stick-kit utilizing the above knowledge.

Figure 2A:
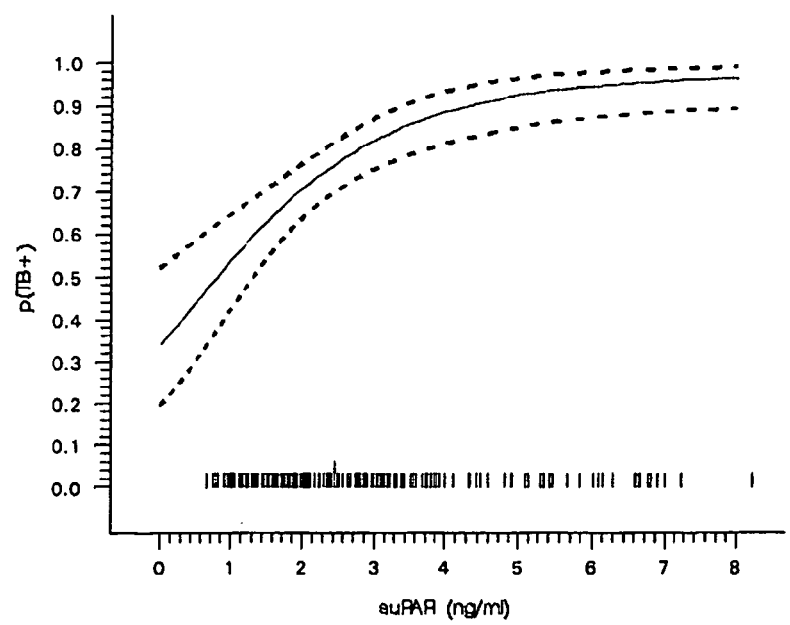

FIG. 2a shows the relationship between suPAR values and the probability of being diagnosed TB positive. The 16 patients who were in treatment for TB at time of inclusion were not included in the analysis. Thus, included in the analysis are the TB positive (TB sputum and culture positive and presumed TB) and the TB negative individuals. Patients with increasing suPAR have higher probability of being diagnosed with active TB (P=0.0001). Patients with suPAR values above 8.3 ng/ml (n=8) are not shown. The blue lines at the bottom indicate the individual patient suPAR values and the high line is the median value. The stippled lines are 95% confidence intervals.

Figure 2B:
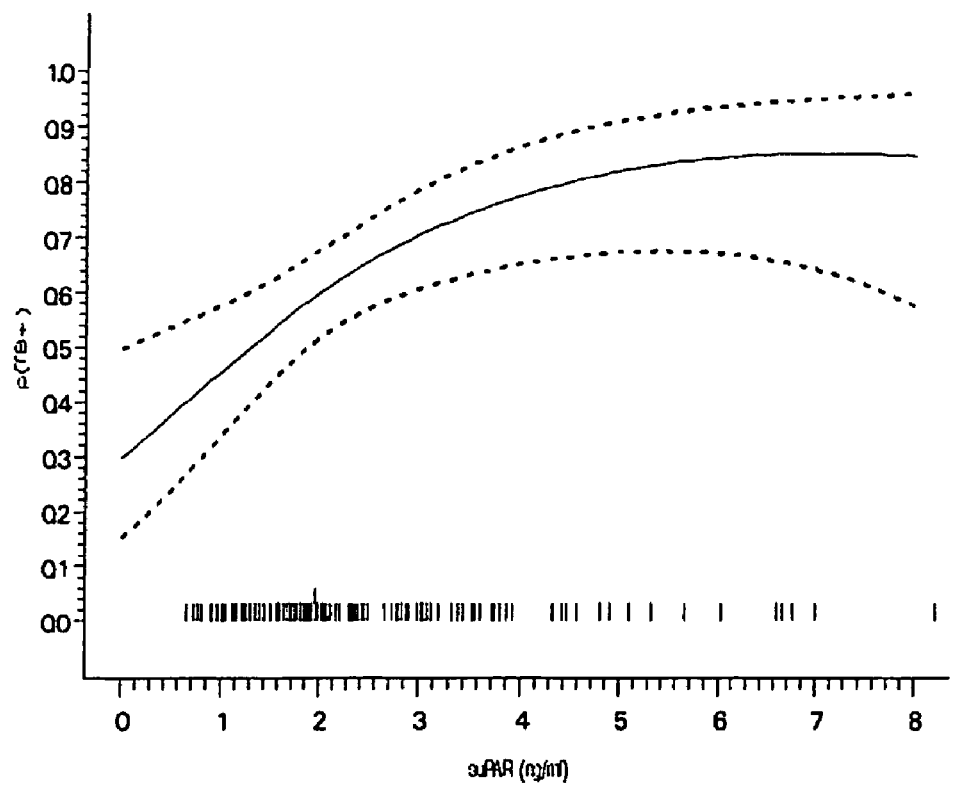

FIG. 2b. Probability of being diagnosed of TB when excluding the TB sputum positive. Patients included in the probability analysis are the 35 culture positive, the 63 presumed TB and the 64 TB negative. Thus, it predicts the probability of all TB suspects excluding the microscopic positive and the 16 patients in treatment at enrollment. Eight samples had suPAR values above 8.5 ng/ml and are not shown. The figure shows that the probability of being TB positive despite a TB negative sputum microscopic analysis increases with increased suPAR levels (p=0.001). The blue lines at the bottom indicate the individual patient suPAR values and the high line is the median value. The stippled lines are 95% confidence intervals.

Figure 2C:
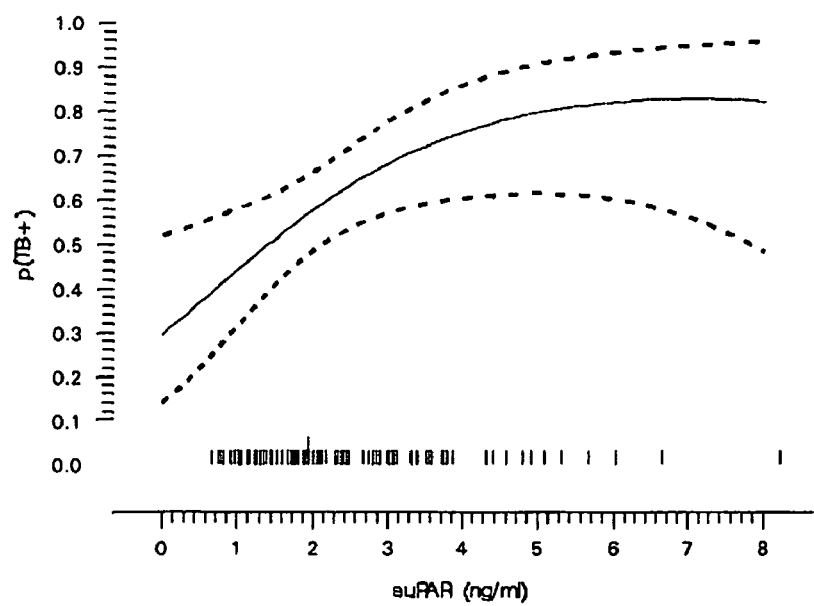

FIG. 2c. The figure is identical to FIG. 2b, except for the exclusion of HIV-1 infected individuals. There was a significant relationship between increasing suPAR and probability of being diagnosed as culture positive or presumed TB (p=0.02). The blue lines at the bottom indicate the individual patient suPAR values and the high line is the median value. The stippled lines are 95% confidence intervals.

Figure 2D:
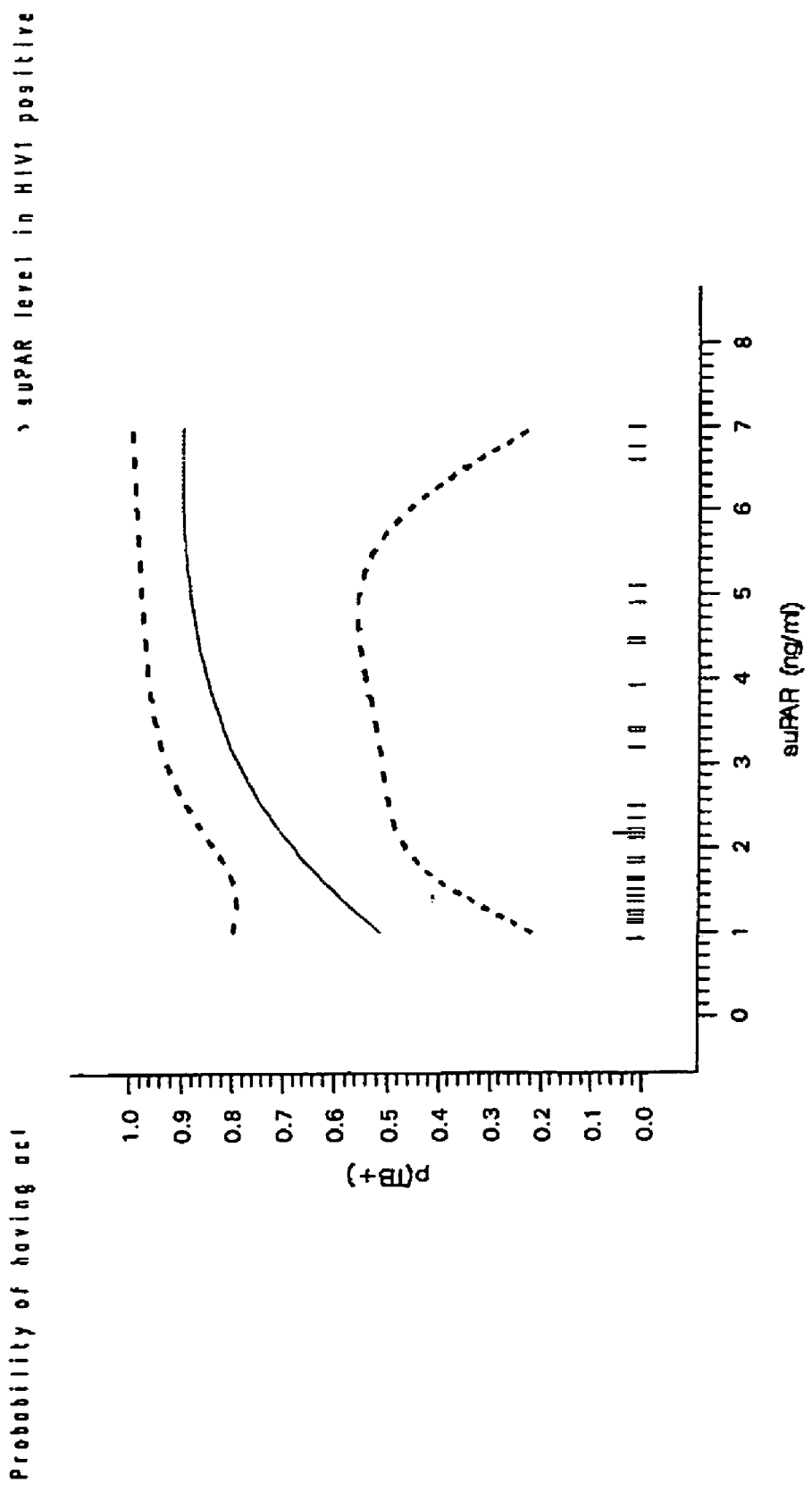

FIG. 2d shows the probability of being TB positive among HIV-1 positive according to suPAR value. p=0.08. There was a trend towards a relationship between increasing suPAR and probability of being diagnosed as culture positive or presumed TB (p=0.08). The blue lines at the bottom indicate the individual patient suPAR values and the high line is the median value. The stippled lines are 95% confidence intervals.

Figure 3:
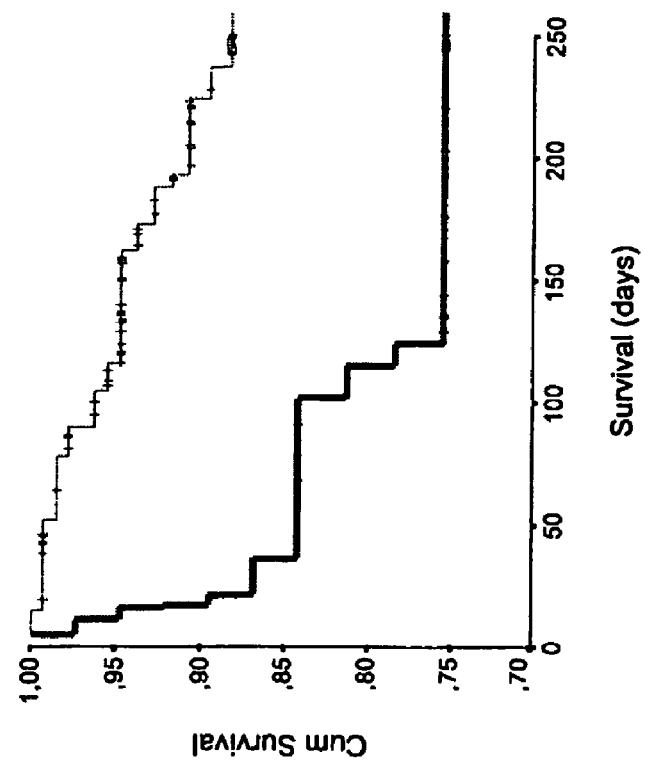
Figure 3:
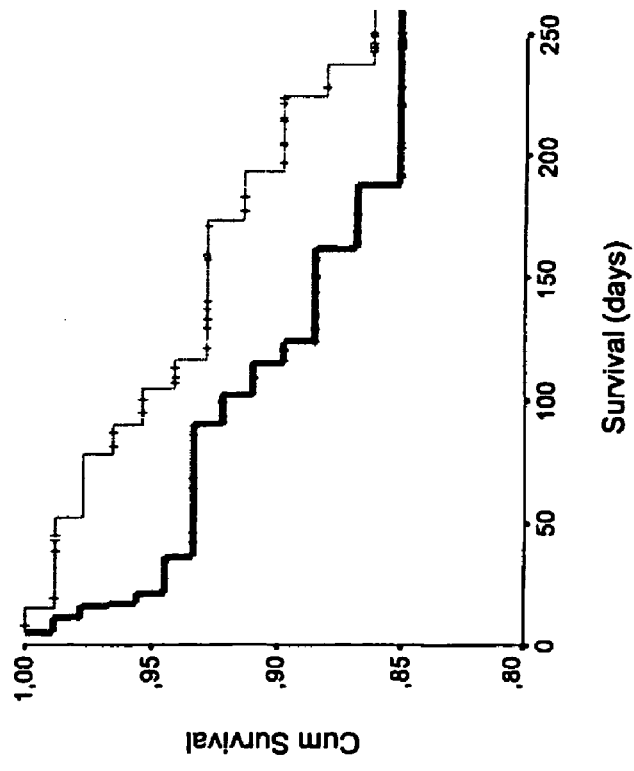

FIG. 3. Kaplan Meier survival curves showing survival among the 182 patients with active TB. The thin line indicates patients with low suPAR and bold line patients with high suPAR. Figure A: There was no significant difference when stratifying patients according to median value. Figure B: Patients with suPAR values above 2 times the median value (i.e., >4.2 ng/ml, n=38), died significantly faster that patients with suPAR below 2 times the median value (n=144), p=0.007, log rank test.

Figure 4:
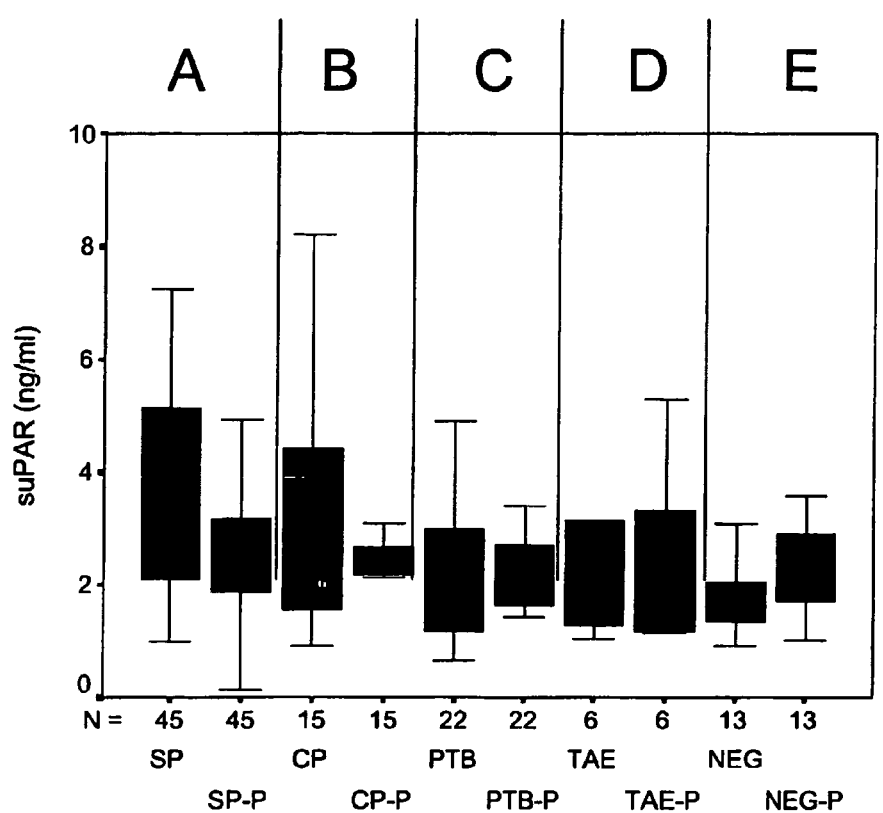

FIG. 4. After treatment, sera were available from 101 individuals. The box-plot shows the pre- and post (post marked with −P) suPAR levels of these 101 individuals. A: TB sputum positive (SP), B: TB culture positive (CP), C: presumed TB (PTB), D: TB positive receiving treatment at enrolment (TAE), and E: TB negative (NEG). For simplicity, the box-plot shows the median (black line in box) and quartiles (box), but not outliers and extremes (cases with values more than 1.5 box lengths from the upper or lower edge of the box).

FIG. 5. Box plots based on the median, quartiles, and extreme values of plasma suPAR levels. A: Control group (median =2.6 ng/ml) and pneumococcal bacteremic patients (median =5.5 ng/ml). suPAR was significantly elevated in patients compared to controls (p=0.001). B: Patients surviving the infection (median =5.0 ng/ml) and patients dying from the infection (median =9.4 ng/ml). The increased level of suPAR in the group of dead patients was statistically significant (p=0.0001). The boxes represent the interquartile range that contains the 50% of values and whiskers extending from the boxes the highest and lowest values, excluding outliers and extremes. Circles (o) represent outliers (1.5 and 3 box-lengths) and stars (*) represent extremes (values more than 3 box lengths).

Figure 6:
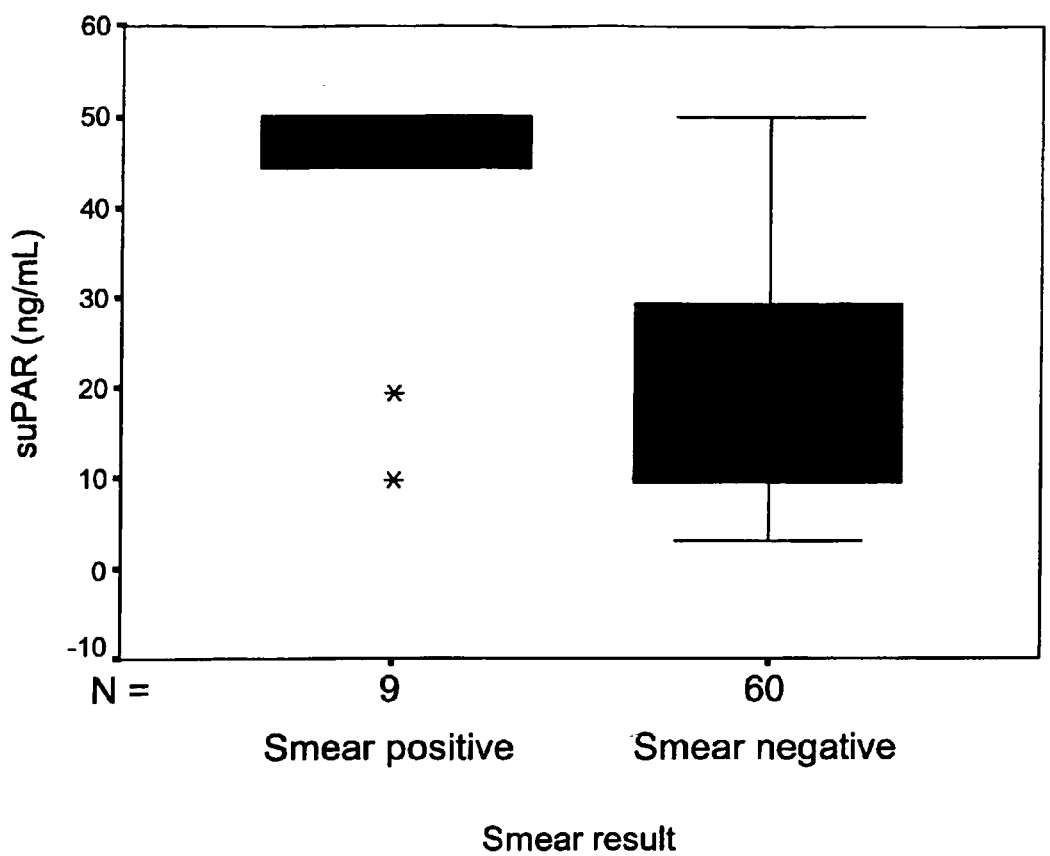

FIG. 6. suPAR levels in individuals with suspected TB according to whether the patients were positive or negative for AFB in direct microscopy.

Figure 7:
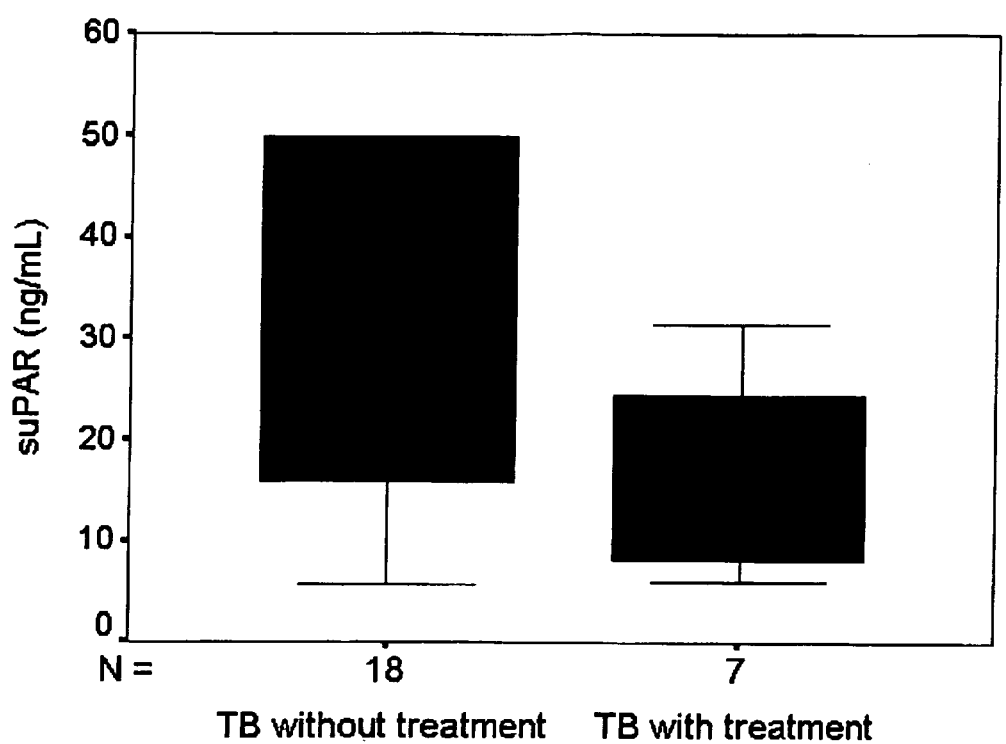

FIG. 7. suPAR levels in untreated and treated TB patients.

Figure 8:
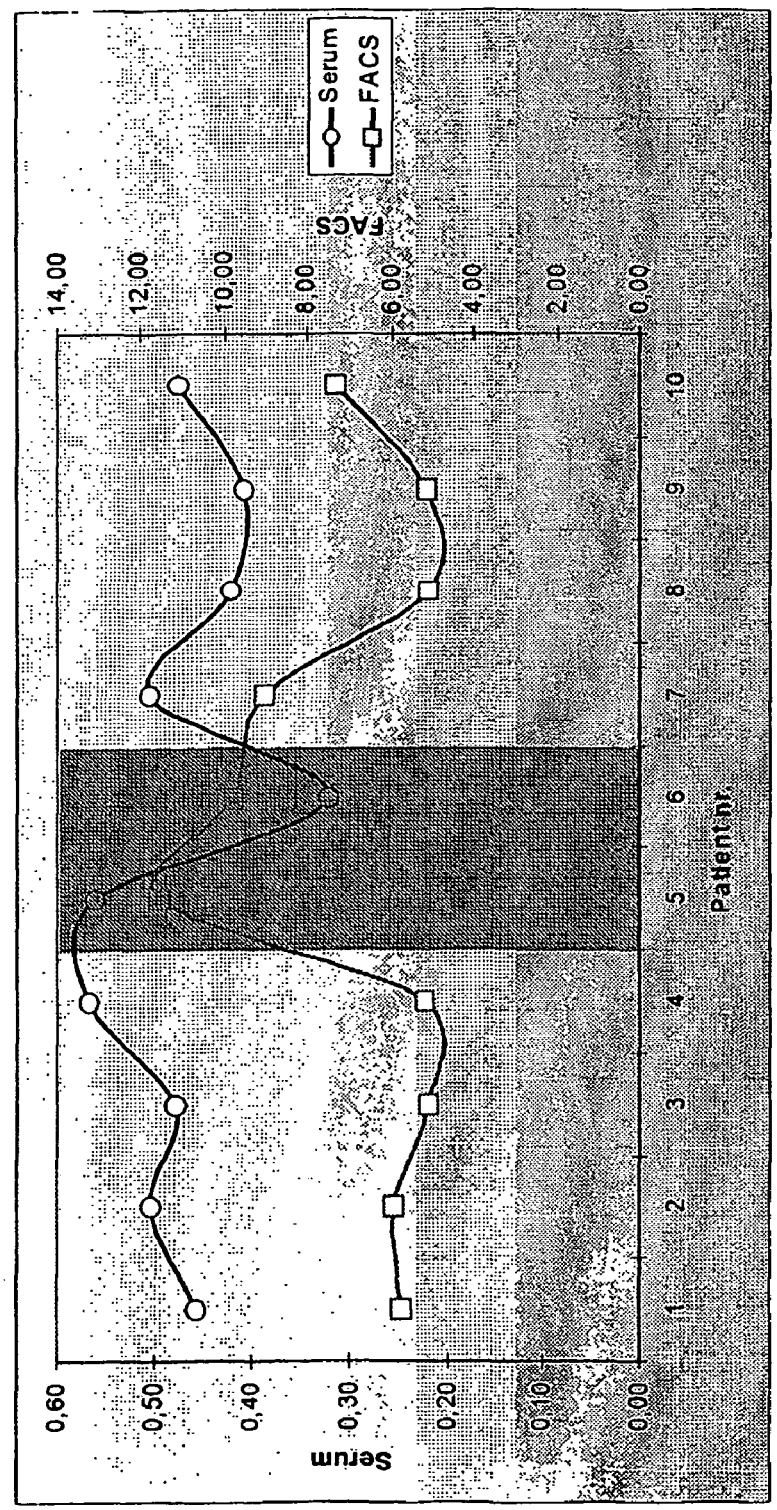

FIG. 8. The Y-axis on the left shows the serum level of suPAR (ng/ml). The Y-axis on the right shows the percentage of cells expressing the uPAR receptor (CD87 positive cells).

DETAILED DESCRIPTION OF THE INVENTION

In the following, the invention is explained in particular with reference to suPAR for reasons of simplicity. This should not be understood as a limitation of the scope of the present invention to suPAR. Furthermore, suitable extrapolations to uPAR and the degradation products of the said two substances lie well within the skill of a person skilled in the art.

The inventors have surprisingly found that the concentration of suPAR, a molecule that is in general known to be involved in cell migration and adhesion, is increased in serum and/or sputum from two major respiratory bacterial pathogens, *Streptococcus pneumoniae* and *Mycobacterium tuberculosis* persons compared with healthy controls.

Major respiratory bacterial pathogens may be selected from
*Streptococcus pneumoniae* (including drug-resistant *S. pneumoniae*)
*Chlamydia pneumoniae* and *Chlamydia psittaci*
*Legionella* spp. *Coxiella burnetii*
*Haemophilus influenzae* Respiratory viruses
Enteric Gram-negative bacilli (specially *Klebsiella* spp.)
Endemic fungi (coccidioidomycosis, histoplasmosis, blastomycosis)b
*Staphylococcus aureus*
*Streptococcus pyogenes*
*Mycoplasma pneumoniae*
*Mycobacterium tuberculosis*
*Pseudomonas aeruginosaa*
*Pneumocystis cariniib*.

The biological fluid sample may be any fluid that can be obtained from humans i.e. sputum, cystic fluid, ascites, blood, serum, plasma, and urine. Urine is preferred due to the fact that it is easy to obtain. When urine is used as the biological fluid sample, the measurement of the marker should be correlated to the total concentration level of the sample, e.g. by correlating the measurement of the marker to the content of creatinine in the sample.

Preferably, the biological fluid sample is stored at a temperature of below 0° C., more preferably from −20° C. to −80° C., until measurement.

The measurement of the marker in the biological fluid sample may be carried out using any available method/device therefore. Examples of such measurement methods/devices are ELISA, RIA (radioimmunoassay), western blotting, TR-FIA (Time-Resolved ImmunoFluorometric Assays), FACS analysis, sticks, etc. Preferred measurement methods/devices are ELISA and sticks.

An ELISA may be carried out in a number of different embodiments, many of which are applicable in the present invention. One ELISA embodiment, which is particularly suitable for use in the present invention, is the one described by[8], and[9] which are included herein by this reference.

The measurement of the marker may be carried out using any suitable stick. Preferably, the stick is a stick comprising an antibody to the marker as a capture agent.

Preferably, the measurement of uPAR in the biological fluid sample is carried out by FACS analysis, western blotting or ELISA.

Preferably, the measurement of uPAR/suPAR degradation products is carried out using western blotting or TR-FIA (Time-Resolved ImmunoFluorometric Assays).

The measurement of uPAR is carried out in biological fluid samples containing uPAR expressing cells, i.e. blood samples.

The measurement value of the level of marker obtained in step (a) may be used to evaluate the state of the subject by comparing the measurement value with the level of the marker in subjects not having a bacterial lung infection with *Streptococcus pneumoniae* or *Mycobacterium tuberculosis*.

As mentioned above, one aspect of the present invention relates to a method of evaluating the progression of the state of a subject suffering from *Streptococcus pneumoniae* or *Mycobacterium tuberculosis* infection.

The measurement values of the level of marker obtained in step (a) may be used to evaluate the progression of the state of the subject by comparing the measurement values with the level of the marker in subjects not infected with tuberculosis or *Streptococcus pneumoniae* and/or by comparing the temporal course of measurement values with that of subjects not infected with tuberculosis or *Streptococcus pneumoniae*.

The invention further relates to an ELISA-kit for evaluating the physical state of a subject suffering from tuberculosis infection comprising a) an immobilised capture agent capable of capturing one or more markers in the form of (i) urokinase plasminogen activator receptor (uPAR), (ii) soluble urokinase plasminogen activator receptor (suPAR), and/or (iii) one or more degradation products of (i) or (ii), and b) a binding partner capable of binding to the marker, the binding partner comprising c) a label system.

The capture agent may be an antibody to the marker.

The binding partner may be an antibody to the marker.

Preferably, the label system is conjugated to the binding partner. The label system may be any conventionally used label system, such as antibody to the binding agent conjugated to an enzyme, e.g. an immunoglobulin-alkaline phosphatase conjugate.

Furthermore, the invention relates to a stick for evaluating the physical state of a subject suffering from tuberculosis or *Streptococcus pneumoniae* infection comprising a) an immobilised capture agent capable of capturing one or more markers in the form of (i) urokinase plasminogen activator receptor (uPAR), (ii) soluble urokinase plasminogen activator receptor (suPAR), and/or (iii) one or more degradation products of (i) or (ii) and b) a binding partner capable of binding to the said marker, the binding partner comprising c) a label system.

The capture agent may be an antibody to the marker.

The binding partner may be an antibody to the marker.

Preferably, the label system is conjugated to the binding partner. The label system may be any conventionally used label system, such as antibody to the binding agent conjugated to an enzyme, e.g. an immunoglobulin-alkaline phosphatase conjugate.

Definitions

In connection with the present invention "uPAR" is defined as any form of uPAR (same as CD87) present on the surface of uPAR expressing cells in biological fluids.

The expression "uPAR expressing cells" refers to all cells expressing uPAR (CD87) such as monocytes, leucocytes, macrophages, and neutrophiles.

In connection with the present invention "suPAR" (soluble uPAR) is defined as any form of uPAR (same as CD87) present in biological fluids in a non-cell-bound form.

"Biological fluids" are defined as any fluid that can be obtained from humans i.e. sputum, cystic fluid, ascites, blood, serum, plasma, and urine.

The expression "degradation product of suPAR or uPAR as used herein means all fragments thereof observed using western blotting or antibodies against suPAR or uPAR. In particular, the said expression includes the D1, D2 and D3 fragments of suPAR.

EXAMPLES

Example 1

Diagnosis of Active TB by Measurement of Serum suPAR

Aim:

To determine whether patients suspected of having active TB has elevated levels of suPAR in serum, i.e. whether suPAR levels may be used to diagnose active TB.

Description of the Experiment

*Mycobacterium Tuberculosis* is an intracellular pathogen that resides predominantly within macrophages. The urokinase plasminogen activator receptor (uPAR) is mainly located on monocytes and macrophages. uPAR is a three domain glycosylated protein (D1-D3) which binds urokinase with high affinity through its D1 domain. The uPAR/uPA complex is involved in plasminogen activation, pericellular proteolysis and tissue remodelling as well as integrin activation, cell adhesion and migration. The uPAR is bound to the cell surface by a GPI anchor, which may be cleaved, resulting in a soluble form of the receptor (suPAR). Soluble forms of uPAR (suPAR) include the full-length receptor (D1-D3) as well as a D2D3 fragment with chemotactic properties[10] and a D1 fragment with unknown function. suPAR has been identified in cell culture supernatants and in biological fluids such as cystic fluid, serum, plasma and urine[11].

Due to the difficulties of diagnosing tuberculosis infection in developing countries and the high mortality caused by the infection, we have investigated suPAR levels among individuals suspected of having active tuberculosis in a cohort in Guinea-Bissau. Here we show that suPAR carries both diagnostic and prognostic information in patients suffering from active tuberculosis.

Population and TB Surveillance

Four suburban areas in Bissau, the capital of Guinea-Bissau, with around 46,000 inhabitants are followed through a demographic surveillance system since 1978. In May 1996, a TB surveillance system was implemented in the area in co-operation with the national TB Hospital, Hospital Raoul Follereau (HRF). All adults permanently or temporarily living in the study area, presenting at any of the 2 health centres with symptoms or signs of active tuberculosis were referred to the hospital for further investigation. Two TB nurses performed visits every third month in houses where TB cases had been found, examining and interviewing the household members in order to find secondary cases. Suspected cases were referred to the TB-hospital for further medical examinations. Patients living in the area, but with TB-treatment initiated elsewhere, were also referred for further investigation and inclusion if identified by the nurses distributing medicine within the national TB programme.

Inclusion Criteria

Criteria for inclusion in the study was one or more of the following symptoms and signs without other explanatory disease: cough >1 month without improvement on antibiotics, fever constantly or periodically for more than 1 month, weight loss, dyspnoea, haemoptysis, nightly sweats or lymphadenopathy. Persons aged <15 years and pregnant women were not included. Consenting patients were investigated clinically, interviewed using standardised questionnaires concerning medical history, socio-demographic and behavioural risk factors, investigated with chest x-ray, direct microscopy on morning sputum on 3 consecutive days, sputum culture and Mantoux-test (using Multiteste®, Bio-Merieux, France). Blood was drawn for testing of HIV-infection, haematology and immunological parameters. Two hundred and sixty-two patients with suspected TB were included in this study. The patients were enrolled between 1996 and 1998. 147 were men and 115 women. Mean age was 41.4 years (range 15-80). Based on the examinations, patients were divided in 4 groups: 1) Patients positive for AFB in sputum direct microscopy (Acid Fast Bacilli, AFB, in direct microscopy) were denoted TB sputum positive. 2) Patients negative in microcopy but positive in culture were denoted TB culture positive. 3) Patients with clinical signs, symptoms and x-ray changes compatible with active intrathoracic TB, but without bacteriological confirmation in sputum direct microscopy or culture, were treated with antibiotics (co-trimoxazole or amoxicillin) and then re-evaluated clinically and with chest x-ray. If there was no improvement and suspicion remained, the patient was assumed to have TB and denoted presumed TB. 4) Patients not diagnosed as having TB were treated according to diagnose (e.g. pneumonia). These patients are denoted TB negative.

TB Treatment

A 4-month intensive phase of daily Directly Observed Treatment (DOT) with standard doses of Ethambutol, Isoniazid, Rifampicin, and Pyrazinamide was followed by a 4-month continuation phase with Ethambutol and Isoniazid collected by the patient at the health centre twice per month. This treatment regimen was recommended for HIV infected individuals by the national TB programme in Guinea-Bissau when the research project was initiated in 1996; for reasons of confidentiality and comparability HIV-positive and HIV-negative individuals received the same treatment. In addition, all patients were given Vitamin B complex and Multivitamins daily. Patients who presented with severe disease were offered hospitalisation if beds were available. In the intensive phase, patients failing to show up for treatment were visited the same day by a nurse and encouraged to continue treatment. Adherence to treatment was verified by pill count and an INH urine test at 2, 5 and 8 months of follow-up; information was noted on treatment cards and forms.

Laboratory Methods

At inclusion, morning sputum samples were collected during three consecutive days by a field assistant and transported in a sealed container at 4° C. the same day to the National Public Health Laboratory (LNSP) in Bissau for direct microscopy and culture. Before culture, samples were digested and decontaminated from non-mycobacterial microorganisms with the lauryl sulphate method. A 0.5-mL aliquot of the homogenised specimen was inoculated into one tube with conventional Löwenstein-Jensen egg medium (LJ) and into one containing a modified LJ with 0.6% pyruvate. The tubes were incubated at 37° C. and examined weekly for 7 weeks. Growth of mycobacteria was confirmed by acid-fast microscopy. Isolates were transported frozen to the Swedish Institute for Infectious Disease Control (SMI) in Stockholm for confirmation.

HIV Testing

Sera were screened for HIV at LNSP using Capillus® HIV-1/HIV-2 (Cambridge Diagnostics, Galway, Ireland) and Enzygnost® Anti-HIV 1+2 Plus (Behring Diagnostics Gmbh, Marburg, Germany). Positive samples were then confirmed with Multispot® HIV-1/HIV-2 (Sanofi Diagnostics Pasteur, Marnes-la Coquette, France). Dual reactive samples were sent frozen to SMI in Stockholm and confirmed using Immunocomb® II Hiv-1&2 Bispot (Orgenics, Yavne, Israel). CD4- and CD8-cell counts were measured using the Immuno-Alkaline phosphatase method[13].

suPAR Measurement

Measurements of suPAR were performed retrospectively on frozen serum samples using a sandwich ELISA. Immunoplates (Maxisorb, Nunc, Denmark) were incubated overnight at 4° C. with a murine monoclonal antibody against human suPAR, R2 (2 µg/mL), in coating buffer (15.1 mM $Na_2CO_3$, 35.7 mM $NaHCO_3$, pH 9.6). After incubating, the wells were washed three times with washing buffer (PBS, 0.1% Tween 20). Non-specific binding was blocked with 2% bovine serum albumin (filtered BSA, Sigma Chemical Co., St Louis, Mo., USA) in phosphate-buffered saline (PBS) for 30 minutes at 37° C. (shaking). After washing three times, the plates were incubated with 10 ul of serum samples diluted with 90 µl buffer, pH 7.4 (7.3 mM $KH_2PO_4$, 50.7 mM $Na_2HPO_4$, 0.1M NaCl, 0.5% phenol red) for one hour at room temperature. The detecting layer consisted of polyclonal rabbit anti-human suPAR (1 µg/mL) in dilution buffer. The secondary antibody used was a monoclonal anti-rabbit immunoglobulin conjugated with alkaline phosphatase (Sigma), diluted 1:2000 in dilution buffer. Thirty minutes after adding the substrate (1 tablet p-nitrophenyl phosphate, Sigma) in 12 mL substrate solution, pH 9.5 (0.1M Tris base, 0.1M NaCl, 5 mM $MgCl_2$), the reactions were stopped using 50 µL/well 1M NaOH and measured at 405 nm. Three laboratory standards were included on all plates. Inter-assay and intra-assay variations were less than 10%. The detection level of suPAR was 0.03 ng/ml.

Statistics

All statistical analyses were performed using the statistical program SSPS, Version 10 or SAS. For comparisons between groups, the Mann Whitney U test or students T-test were used. The probability of suPAR to predict active TB was assed using a logistic regression model. All probability-tests were performed as likelihood ratio tests. Difference between Kaplan-Meier curves was analysed by the log-rank test. The ability of serum suPAR to predict mortality in the context of other known prognostic markers was formally assessed using the Cox proportional hazards model. All test were conducted as partial likelihood ratio tests. The statistical model allowed for other than linear relationship of suPAR to mortality. The linear relationship was sufficient. A significance level of 5% was used. Cox regression analysis was carried out from time of inclusion and until treatment termination or censoring due to death (N=30), beginning of the war in Guinea Bissau (Jun. 6, 1998) (N=50), or loss to follow-up because the patient moved back to the rural areas (N=23). The sixteen patients, who were receiving TB treatment at time of enrolment, were not included in the survival analysis since treatment may have affected their suPAR level. Regarding HIV-status, patients dually infected (both HIV-1 and HIV-2 positive) were included in the analyses as HIV-1 positive since dually infected individuals have been found to have the same risk and severity of TB infection as HIV-1 individuals.

Ethics

Pre and post-counselling for both HIV result and TB disease was offered to all included by the doctors in charge of the study. The subjects were informed in writing in Portuguese and verbally in their own language before being enrolled in the study. Informed consent was obtained from all patients. The study was approved by the Ministry of Public Health in Guinea-Bissau, and by the Central Ethical Committee of Denmark.

Results:

All 262 individuals had measurable suPAR and the median suPAR level was 2.1 ng/ml (range 0.66-18.7 ng/ml) at enrolment. There was no correlation between age and suPAR ($p=0.9$) and no difference in suPAR levels between men and women ($p=0.87$)(table 1). Of the 262 individuals, 16 were already known to have active TB and were under appropriate treatment at time of enrolment. Of the remaining 244 individuals, active TB was diagnosed in 182, who consequently entered the 8-month treatment regimen. Among these, 84 were found positive by direct microscopy of sputum (TB sputum positive) and 35 cases were negative in direct microscopy but positive in culture (TB culture positive) and 63 were diagnosed on clinical and radiological grounds (presumed TB). The remaining 64 were diagnosed as having pneumonia or bronchitis (TB negative).

suPAR is Elevated in Tuberculosis Infection

Figure 1:
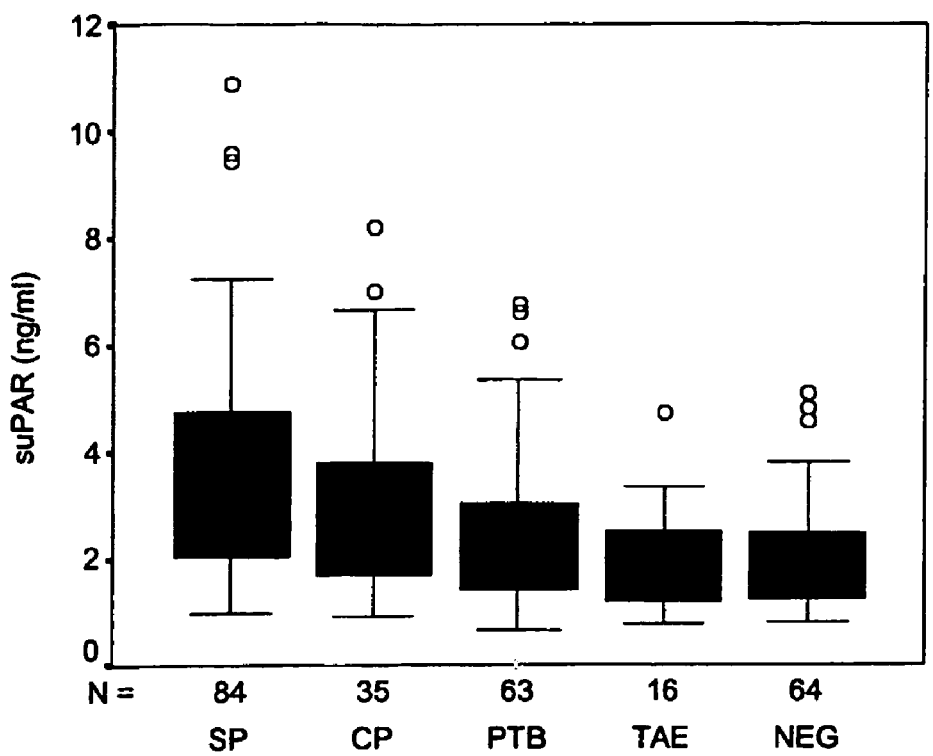
FIG. 1. suPAR levels among TB sputum positive (SP), TB culture positive (CP), presumed TB (PTB), TB positive receiving treatment at enrolment (TAE), and TB negative (NEG). The box-plot shows the median (black line in box), quartiles (box) and outliers (cases with values between 1.5 and 3 box lengths from the upper or lower edge of the box), but not extremes (cases with values more than 3 box lengths from the upper or lower edge of the box).

The suPAR levels were significantly higher among the TB positive patients (TB sputum positive, TB culture positive and presumed TB, N=182) compared to the TB negative patients (N=64)($p<0.001$) (FIG. 1). The suPAR levels were elevated in the 84 TB sputum positive ($p<0.001$), and in the 35 TB culture positive ($p=0.005$) compared to the 64 TB negative. There was a trend towards elevated suPAR levels in the 63 diagnosed presumed TB compared to the TB negative ($p=0.06$). No difference was observed in suPAR levels between the 16 patients who had received treatment prior to inclusion in the study and the TB negative ($p=0.72$, t-test). The suPAR levels are shown in FIG. 1.

suPAR Carries Diagnostic Value for TB

When including all enrolled in the study, there was a significant higher probability of being diagnosed with TB with increasing suPAR. This is shown as a probability plot in FIG. 2a. Due to the difficulties of diagnosing the sputum negative individuals, the most interesting analysis was whether suPAR carried diagnostic value in the 162 sputum negative individuals, i.e., when excluding the 84 TB sputum positive. We found that there was an increasing risk of being diagnosed as TB culture positive or presumed TB with increasing suPAR levels ($p=0.001$, FIG. 2b). Because HIV-1 infection affects the suPAR level, we made the same analysis for the 130 HIV-1 negative individuals (76 HIV-1 negative TB culture positive or presumed TB and 54 HIV-1 negative TB negative patients) and found the same association between increasing probability of being diagnosed as TB positive with increasing suPAR levels ($p=0.02$, FIG. 2c).

Higher suPAR Level at Inclusion Among the TB Bacteriological Patients who Died During Follow-up Patients were followed from time of inclusion and were treated for an 8-month period. Thirty died during the follow-up with a median suPAR level at inclusion of 3.26 (range 1.04-18.70), which was significantly higher than among the 232 survivors (median suPAR 2.12, range 0.66-16.22) ($p=0.02$). Among the 119 bacteriologically confirmed TB patients (TB sputum and TB culture positive), ten died during the follow up. Those who died had significantly higher suPAR levels (median 5.98 ng/ml, range 1.3-18.3) than the survivors (median 3.04 ng/ml (Range 0.9-14.7)) (Mann Whitney, $p=0.022$). Among the 63 presumed TB, 13 died during the treatment period. The suPAR level at inclusion of the 13 who died was median 2.35 ng/ml (range 1.0-6.6) versus median 2.12 ng/ml (range 0.7-6.6) among survivors ($p=0.45$). Among the 64 TB negative, 7 died during the follow-up with median suPAR of 3.32 (range 1.43-18.70) and 57 was alive at follow-up having a median suPAR of 1.17 ng/ml (range 0.81-16.22) ($p=0.04$). When dividing the patients into 4 equally sized groups based on suPAR level, there was a trend towards higher mortalitity among patients in the highest suPAR quartile compared to the lowest suPAR quartile (5/65 vs. 13/65, $p=0.07$)(table 1).

Kaplan Meier Analysis on Patients with Active TB

There was no difference in survival among patients with active TB (TB sputum, TB culture or presumed TB, n=182) when dividing patients by median suPAR value (FIG. 3A). Patients with more than two times the median value, i.e., patients having higher than 4.2 ng suPAR/ml serum (n=38) were at increased risk of dying during the follow up compared to patients having suPAR values below 4.2 ng/ml (N=144) (MR=3.05 per ng suPAR increase, $p=0.007$), FIG. 3B.

suPAR Level as Predictor for Outcome of HIV-1 Infection 47 were found to be HIV-1 or dually infected at time of inclusion. The HIV-1 infected had a median suPAR level of 2.34 ng/ml (range 0.92-18.7). Of the 47 patients, 13 died during the follow-up (median suPAR 3.43, range 1.15-18.70). These patients had significantly higher suPAR value than the 34 patients alive at study censoring (median suPAR 2.05. range 0.92-6.88) ($p=0.015$, Mann Whitney). Cox regression analysis on HIV-1 infected showed that suPAR was significantly associated with survival in this subgroup ($p<0.001$, MR=1.53). There was a similar difference in suPAR levels among the 66 HIV-2 infected individuals (median suPAR 2.44, range 0.91-18.30), of whom 7 died during follow-up (median suPAR 3.32, range 1.04-18.3), 59 survived (median suPAR 2.44, range 0.91-14.71) though the difference was not significant due to the smaller number of deaths ($p=0.64$). There was no significant difference between suPAR levels in patients with TB with or without HIV infection or between the number of HIV 1 or 2 infected between the different TB diagnostic groups (Table 2).

SuPAR Serum Level is Correlated to Survival in Cox Regression Analysis

Excluding the 16 patients who had received treatment at enrolment, 182 patients diagnosed with active TB were followed for a period of up to 8 months after initiation of treatment and 23 died. In univariate Cox regression analyses, suPAR levels were significantly associated with death during treatment (increase in mortality rate ratio (MR)=1.18 per ng suPAR increase, $p=0.01$), as was HIV-1 infection (MR=2.66, $p=0.023$) and status as TB positive based on clinical and radiological grounds (presumed TB) ($p=0.03$). When treating all TB positive patients equally regardless of their HIV-status we found no effect of diagnostic method on time to death when taking into account the level of suPAR ($p=0.43$). Neither HIV-2 positivity ($p=0.63$), age ($p=0.72$), sex ($p=0.19$) or log 10 transformed CD4 T cell counts (p=0.42) were found to be significantly associated with survival during the follow-up period.

In a multivariate Cox analysis including all significant factors, all remained significant the MR being 3.9 (p=0.003) for bacteriological negative TB (presumed TB) compared with the bacteriological positive TB patients, MR=2.1 (p=0.12) for HIV-1 positivity compared with HIV-1 negative TB patients, and 1.28 (p<0.001) per ng suPAR increase.

When excluding the HIV-1 positive patients, 14 died among the remaining 149 TB patients. Among these HIV-1 negative patients with active TB, suPAR still retained predictive power (RR=1.14, p=0.05). Thus, we observed the same dose/response (suPAR/time to death) relationship when excluding the HIV-1 positive patients.

Discussion

*Mycobacterium Tuberculosis* affects the lives of millions of people worldwide and 3 millions are estimated to die from the disease every year. In this example we find, for the first time, that the suPAR molecule holds diagnostic and prognostic value in TB infection.

In this example, 32 percent of the 262 individuals suspected to be TB positive were found positive by direct microscopy. These TB sputum positive had higher levels than those diagnosed by culture (TB culture positive) or clinical diagnosed (presumed TB). All these patients had higher suPAR levels than the TB negative.

Due to the difficulties of diagnosing active TB in patients negative in microscopy, an important question in this study was whether suPAR may have diagnostic value in individuals in who suspicion of TB remains. We found that there was an increasing probability of patients being diagnosed as having active TB by culture (culture positive) or by clinical investigation (presumed TB) with increasing suPAR level. The TB negatives were included in the study on suspicion of TB due to related symptoms and were regarded as having pneumonia after negative tests in culture and clinical examination and treated with antibiotics post entry. We do not know whether the suPAR level may be higher among the TB negatives compared to a control group of healthy individuals. However, there was a marked difference between the TB negatives and the groups diagnosed as having active TB indicating that pneumonia would not cause a major increase in suPAR.

Sixteen patients were receiving appropriate TB treatment at time of inclusion. The serum level of suPAR in these patients was significantly lower than in the patients diagnosed with TB after inclusion, and comparable to the TB negative. This indicates that the suPAR level may drop following treatment and that suPAR can be used to monitor the effect of treatment.

SuPAR was prognostic for survival in this cohort. Among the TB sputum and culture positive, 10 died during the follow-up, and these individuals had significantly higher suPAR values at inclusion. Using Cox regression analysis, suPAR was significantly associated with survival among the 182 patients diagnosed with TB. We have previously shown suPAR to be prognostic for HIV-1 disease progression and this observation was confirmed in this study. When excluding the HIV-1 and dually positive, suPAR still remained significantly associated with survival among the patients with active TB. Another factor significantly associated with survival in Cox regression analysis is type of TB diagnosis. Patients diagnosed of active TB by clinical examination only (presumed TB) were at larger risk of dying during the follow up which probably is due to the delayed treatment. The observation of highest suPAR level in the TB sputum positive followed by TB culture positive and TB individuals negative in bacteriological assays (presumed TB) indicated that suPAR might be correlated to the tuberculosis bacterial load. As increased suPAR levels are likely to reflect increase uPAR expression on cell surface Mustjoki our findings suggests that either suPAR and/or uPAR may be involved in the pathogenesis of tuberculosis infection. The initial interaction between *M. Tuberculosis* and host macrophages is an important first step in the pathogenesis of tuberculosis. This step is mediated by specific monocyte/macrophage receptors and ligands present on the surface of TB. Several macrophage receptors has been reported to mediate binding to *M. Tuberculosis*, including complement receptors CR1, CR3 and CR4, glucan receptor, mannose receptor lipopolysacharide receptor and toll-like receptors. However, none of these receptors have been demonstrated to be essential for the macrophage/*M. tuberculosis* interaction. The involvement of CR3 in tuberculosis entry have been further enlightened by the use of CD11b knock-out mouse models which show a 60% reduction in tuberculosis infectivity but no effect on intracellular replication. uPAR have been shown to complex with CR3 (mac-1, CD11b/CD18). uPAR bind CR3 through CD11b (reviewed in 14 resulting in activation of the complex. Thus, one possible reason for the diagnostic and prognostic role of suPAR in TB could be due to involvement and enhancement of uPAR/CD11b tuberculosis cell entry. Another possibility is that uPAR become upregulated by intracellular TB replication and thereby reflects the number of infected cells. Apart from HIV and now tuberculosis infection, the serum level of suPAR is also a prognostic marker for overall survival in patients suffering from ovarian and colorectal cancer and for the response to therapy in leukaemia[15],[11]. Another possible suPAR elevator is *borrelia burgdorferi*, as a resent in vitro study showed increased levels of uPAR on monocytic cells following infection. To be able to compare data between individual studies in cancer, TB and HIV infection, it is necessary to develop a reproducible and commercially available suPAR assay. The assay used in this study is comparable to the assay used in our previous study of suPAR as prognostic factor in HIV progression[7] and described in the study by Stephens et al.[16]

In conclusion, we find that suPAR is elevated in patients with active TB and that patients with high suPAR level has a higher risk of dying during the treatment period.

TABLE 1

Patients divided into four equally sized groups according to their suPAR level. Brackets show number of patients that died during follow-up.

| | First quartile Median 1.21, range 0.66-1.51 N = 65 | Second quartile Median 1.84, range 1.51-2.18, N = 66 | Third quartile Median 2.90, range 2.23-3.43, N = 66 | Forth quartile median 5.10, range 3.52-18.70 N = 65 | Total N |
|---|---|---|---|---|---|
| TB sputum positive | 9 (1) | 17 (1) | 27 (1) | 31 (6) | 84 (9) |
| TB culture positive | 6 (0) | 10 (0) | 7 (0) | 12 (1) | 35 (1) |
| Presumed TB | 16 (2) | 17 (4) | 18 (4) | 12 (3) | 63 (13) |
| TB negatives | 27 (2) | 17 (1) | 12 (2) | 8 (2) | 64 (7) |
| Treatment at inclusion | 7 (0) | 5 (0) | 2 (0) | 2 (0) | 16 (0) |
| Total | 65 (5) | 66 (6) | 66 (7) | 65 (12) | 262 (30) |
| HIV-1 positive | 10 (2) | 11 (0) | 12 (5) | 14 (6) | 47 |
| HIV-2 positive | 14 (1) | 16 (2) | 18 (1) | 18 (3) | 66 |

TABLE 1-continued

Patients divided into four equally sized groups according to their suPAR level. Brackets show number of patients that died during follow-up.

|  | First quartile Median 1.21, range 0.66-1.51 N = 65 | Second quartile Median 1.84, range 1.51-2.18, N = 66 | Third quartile Median 2.90, range 2.23-3.43, N = 66 | Forth quartile median 5.10, range 3.52-18.70 N = 65 | Total N |
| --- | --- | --- | --- | --- | --- |
| Age (median) | 44 | 39 | 39 | 36 | |
| Men | 37 | 36 | 38 | 36 | 147 |
| Women | 28 | 30 | 28 | 29 | 115 |

TABLE 2

The table illustrates the number (and percentage of TB diagnostic group) and suPAR (median, range) of HIV infected among patients grouped according to TB diagnosis.

| Diagnose, N (% of group) suPAR median (range) | HIV-1 infected | HIV-2 infected | HIV negative | Dead |
| --- | --- | --- | --- | --- |
| Sputum positive, N = 84 3.17 (0.99-18.30) | 11 (13.1%) 3.11 (1.8-10.9) | 24 (28.6%) 3.28 (1.3-18.3) | 49 (58.3%) 3.09 (1.0-13.4) | 9 (10.7%) 5.86 (1.3-18.3) |
| Culture positive, N = 35 2.41 (0.91-8.21) | (25.7%) 2.23 (1.2-7.0) | 6 (17.1%) 3.07 (0.9-6.7) | 20 (57.1%) 2.25 (1.1-8.2) | 1 (2.9%) 7.01 |
| Presumed TB, N = 63 2.13 (0.66-6.77) | 13 (20.6%) 2.50 (1.2-6.8) | 19 (30.1%) 2.08 (1.0-6.0) | 31 (49.2%) 2.13 (0.7-5.3) | 13 (20.6%) 2.35 (1.0-6.8) |
| Treat at enrol, N = 16 1.62 (0.77-7.30) | 4 (25%) 1.79 (1.4-3.3) | 1 (6.3%) 1.53 | 68.8%) 1.29 (0.8-7.3) | 0 |
| TB negatives, N = 64 1.73 (0.81-18.70) | 10 (17.9%) 1.67 (0.9-18.7) | 16 (25.2%) 2.15 (1.0-4.6) | 38 (56.9%) 1.63 (0.8-16.2) | 7 (10.9%) 3.32 (1.4-18.7) |

Example 2

The serum level of soluble urokinase receptor is elevated in Tuberculosis patients, predicts mortality during treatment and may be used to monitor TB treatment efficacy.

Objective:

To investigate whether the serum level of soluble urokinase plasminogen activator receptor (suPAR) carries prognostic information in individuals infected with *Mycobacterium tuberculosis* during the treatment period and whether it may be used to monitor TB treatment efficacy.

Design:

suPAR was measured by ELISA in 262 individuals at time of enrolment into a cohort based on suspicion of active tuberculosis and in 101 individuals after 8-months of follow-up. The 262 individuals are the same as investigated in Example 1.

Results:

The suPAR levels were elevated in patients with active TB compared to TB negative individuals (p<0.001). suPAR levels were highest in patients positive for TB in direct microscopy (N=84, median suPAR 3.17 ng/ml, p<0.001), followed by patients negative in direct microscopy but culture positive (N=35, median suPAR 2.41 ng/ml, p=0.005) and by patients diagnosed on clinical grounds (N=63, median suPAR 2.13 ng/ml, p=0.06) compared to 64 TB negative individuals (median suPAR 1.73 ng/ml). During the 8-month treatment period, 23 TB cases died. In a multivariate Cox model controlling for HIV status, age, sex, CD4 count and type of TB diagnosis, the mortality increase per ng suPAR was 1.25 (95% Cl 1.12-1.40). After treatment, suPAR levels had decreased to the levels of TB negative individuals.

Conclusions: suPAR levels are elevated in TB patients and associated with mortality. Furthermore, suPAR is a marker of treatment efficacy.

Study Population and Methods:

Inclusion Criteria and Laboratory Methods

The subjects included in this study are the same as in example 1. The difference between the study described here and the one in example 1, is that this study investigates the role of suPAR as marker during the 8 months of therapy.

Furthermore, during the treatment period, 30 patients died. After 8 months of follow-up, a second blood sample was drawn. Of the 262 individuals included in this study, 101 individuals were available for a second bleeding.

Statistics

For comparisons between groups, the Mann-Whitney U-test was used except for comparisons between pre- and post TB treatment suPAR levels in which cases paired samples t tests were used. The difference between Kaplan-Meier curves was analysed by the log-rank test. The ability of serum suPAR to predict mortality, accounting for other known prognostic markers, was formally assessed using a Cox proportional hazards model allowing for non-linear relationships between suPAR and mortality. All tests were conducted as partial likelihood ratio tests. The analysis of time to death was carried out from time of inclusion to the first of the events: treatment termination, 8 months follow-up, death (N=30), beginning of the war in Guinea Bissau which influenced treatment (N=50), or loss to follow-up because the patient moved back to the rural areas (N=23). The sixteen patients who were receiving TB treatment at inclusion were not included in the survival analysis since treatment may have affected their suPAR level. Regarding HIV-status, patients dually infected (both HIV-1 and HIV-2 positive, N=19) were included in the analyses as HIV-1 positive since dually infected individuals have been found to have the same risk and severity of TB infection as HIV-1 individuals. Statistical analyses were performed using the program SSPS, Version 10 or SAS version 8.1. A level of 5% was used for significance.

Ethics

All subjects received written information in Portuguese and verbal information given in their local ethnic language, prior to enrolment. Informed consent was obtained from all patients. The study was approved by the Ministry of Public Health in Guinea-Bissau, and by the Central Ethical Committee of Denmark.

Results:

All 262 individuals had measurable suPAR and the median suPAR level was 2.1 ng/ml (range 0.66-18.7 ng/ml) at enrolment. There was no correlation between age and suPAR ($p=0.9$) or in suPAR levels between men and women ($p=0.87$) (table 1). Of the 262 individuals, 16 were already known to have active TB and were under appropriate treatment at time of enrolment. Of the remaining 246 individuals, active TB was diagnosed in 182, who consequently entered the 8-month treatment regimen. Among these, 84 were TB sputum positive, 35 cases were TB culture positive, and 63 were diagnosed as presumed TB. The remaining 64 were diagnosed as TB negative. During the treatment period 30 cases died, of these were 7 TB negative (Table 1).

suPAR is Elevated in Tuberculosis Infection

The suPAR levels were significantly higher among the TB positive patients (TB sputum positive, TB culture positive and presumed TB, N=182) compared to the TB negative patients (N=64, $p<0.001$). The suPAR level seems to correlate to the number of mycobacterium in sputum as the highest suPAR levels were found among the 84 TB sputum positive ($p<0.001$), followed by the TB culture positive ($p<0.001$), and the presumed TB ($p=0.06$) when comparing to the suPAR levels found in the 64 TB negatives as shown in FIG. 1. No difference was observed in suPAR levels between the 16 patients receiving TB treatment at time of enrolment and the TB negative ($p=0.72$). Grouping of patients into quartiles according to suPAR level is shown in table 1.

Kaplan Meier Analysis on Patients with Active TB

There was no significant difference in the survival rate among patients with active TB (TB sputum, TB culture or presumed TB, n=182) when dividing patients by median suPAR value (FIG. 3A). Patients with high suPAR (more than two times the median value, i.e., patients having higher than 4.2 ng suPAR/ml serum (n=38)) died significantly faster following enrolment, compared to patients below 4.2 ng/ml (N=144, $p=0.007$), FIG. 3B.

suPAR SERUM Level is Correlated to Survival in Cox Regression Analysis

Excluding the 16 patients who had already started treatment at time of enrolment, 182 patients diagnosed with active TB were followed for a period of up to 8 months after initiation of treatment, 23 of these died. In univariate Cox regression analyses, suPAR levels were significantly associated with death during treatment, the increase in the mortality rate ratio (MR) being 1.18 per ng suPAR increase (95% CI: 1.06-1.30), as was HIV-1 infection (MR=2.71, 95% CI: 1.16-6.29) and status as TB positive diagnosed on clinical and radiological grounds (presumed TB) (MR=2.48, 95% CI: 1.09-5.66). When treating all TB positive patients equally regardless of their HIV-status and adjusting for the level of suPAR we found no effect of diagnostic method on mortality ($p=0.43$). Neither HIV-2 positivity ($p=0.63$), age ($p=0.72$), sex ($p=0.19$) or log 10 transformed CD4 cell counts ($p=0.42$) were found to be significantly associated with survival.

All factors found to be significant in univariate analyses remained significant in the multivariate Cox analysis. Controlling for TB diagnosis (presumed TB compared with TB-cases positive in direct microscopy or culture, MR=3.5 (95% CI: 1.39-8.67)), and HIV status (HIV-1 positive compared with HIV-1 negative TB patients, MR=2.5 (95% CI: 1.07-5.99)), the increase in mortality per ng suPAR was MR=1.25 (95% CI: 1.12-1.40).

When excluding the HIV-1 positive individuals, 14 died among the remaining 149 TB patients during the follow-up. Among these 149 TB patients, suPAR still retained predictive power (MR=1.14, 95% CI: 1.00-1.31). Thus, the positive association between suPAR and death was similar in HIV-1 positive and HIV-1 negative subjects.

suPAR Level as Predictor for Outcome Among the HIV-1 or -2 Infected Individuals

We have previously shown that suPAR is a strong prognostic factor for HIV-1 progression. In the present study, 47 of the 262 individuals suspected of having TB were found to be HIV-1 positive at time of inclusion and 13 died. Univariate Cox regression analysis on the HIV-1 infected showed that suPAR was significantly negatively associated with survival (n=47, MR=1.53 per ng suPAR increase, 95% CI: 1.22-1.92). No other parameters (age, sex, TB diagnosis or CD4 count) were significantly associated with survival in this subgroup. Sixty-six of the 262 individuals were HIV-2 positive at inclusion (not including the dually infected) of whom seven died during follow-up. There was a similar effect of suPAR on survival (n=66, MR=1.13, 95% CI: 0.97-1.32) although the difference was not significant due to the smaller number of deaths. Neither age, sex, TB diagnosis nor CD4 counts were significantly associated with survival in the HIV-2 group. There were no significant differences in suPAR levels in TB patients with or without HIV infection, or between HIV-1 and -2 infected individuals in the different TB diagnostic groups.

Treatment was associated with a decrease in suPAR levels

Of the 262 individuals included in this study, serum samples were available from 101 patients after 8 months of treatment. At inclusion, 45 were diagnosed as TB sputum positive, 15 as TB culture positive, 22 as presumed TB, 6 received treatment at enrolment, and 13 as TB negatives. The pre- and post treatment suPAR levels for these individuals are shown in FIG. 3. Treatment was associated with a significant decrease in suPAR among the 45 TB sputum positive (95% CI: −2.07−−0.56 ng/ml) and a non-significant decrease for the 15 TB culture positive, (95% CI: −2.12−0.24 ng/ml). No difference in pre- and post treatment suPAR values was observed for presumed TB (95% CI: −0.81-0.84) or for patients receiving treatment at enrolment (95% CI: −3.3−3.1). An increase in suPAR was observed after treatment among the 13 TB negatives (3 HIV-2 positive and 10 HIV negative ($p=0.041$, 95% CI: 3.31−1.33 ng/ml). The increase was most prominent among the three HIV-2 positive. The post treatment suPAR levels did not differ between the different diagnostic groups (FIG. 3).

Discussion

*Mycobacterium Tuberculosis* affects the lives of millions of people worldwide and 2 millions are estimated to die from the disease every year. In the present example, we found that suPAR levels were elevated in TB patients, correlates to type of TB diagnosis and carries prognostic value. Furthermore, treatment was associated with decreased serum suPAR levels.

suPAR was found to be significantly higher among the TB cases compared to the non-TB cases. Furthermore, the highest suPAR levels were found in TB cases positive in direct microscopy, followed by cases negative in direct microscopy but positive in culture, and then the TB cases negative in both direct microscopy and culture. Given that culture is a more sensitive method than direct microscopy in diagnosing presence of AFB in sputum, these results may indicate that the level of suPAR in blood is correlated to the number of bacteria in sputum and consequently the bacterial load in the bronchi. The enhanced suPAR levels may be a result of mobilisation of macrophages into the bronchi. Adherence and migration of monocytes involves a functional interaction between uPAR and integrins as also supported by studies in uPAR knock-out mice {May, Kanse, et al. 1998 MAY 1998/id}. The best-described uPAR/integrin interaction is between uPAR and CD11b/CD18 (complement receptor 3 or MAC-1) {Simon, Rao, et al. 1996 14/id}. After this patent was filed, Juffermans and coworkers showed concurrent upregulation of uPAR and CD11b during experimental endotoxemia using LAM, a cell wall component of *M. Tuberculosis*[17]. Interestingly, CD11b/CD18 has also been shown to mediate attachment of *M. tuberculosis*[18] to macrophages suggesting that TB may exploit this upregulation to adhere and infect recruited macrophages. Thus, we propose that this may be a new target for *M. tuberculosis* interaction.

Using Cox regression analysis, suPAR was found to be significantly associated with survival among the 182 patients diagnosed with TB. In Guinea-Bissau, the prevalence of HIV is higher among TB cases compared to healthy controls. We have previously shown suPAR to be a strong prognostic marker for HIV-1 disease progression[11], and this observation was confirmed in the present study. However, even when excluding the HIV-1 infected, suPAR still remained significantly associated with survival among the patients with active TB.

Eight months of treatment lead to a significant decrease in suPAR levels, resulting in similar levels between those diagnosed with or without TB at inclusion. Also, sixteen patients were already receiving appropriate TB treatment at the time of inclusion. The serum suPAR levels in these patients were significantly lower than in the patients diagnosed with TB after inclusion, and comparable to the TB negative. These observations show that suPAR measurement may be a useful tool for monitoring treatment response in TB patients.

suPAR is elevated and prognostic for outcome in HIV-1 infection. This study has shown that the serum level of suPAR is elevated in TB patients and that the pre-treatment level is positively associated with mortality in patients receiving treatment for TB.

Conclusions:

The serum level of soluble urokinase receptor (suPAR) is elevated in patients with active tuberculosis and highest in patients who are sputum positive in microscopic analysis. suPAR was found to positively associated with mortality in TB patients during treatment, even when excluding the HIV-1 co-infected for whom suPAR is known to be a very strong prognostic marker. Following treatment, sputum positive patients had significantly lower suPAR levels suggesting suPAR could be used to monitor TB treatment efficacy.

Example 3

The Plasma Level of Soluble Urokinase Plasminogen Activator Receptor is Elevated in Patients with *Streptococcus pneumoniae* Bacteremia and Carries Strong Prognostic Value.

*Streptococcus pneumoniae* (*S. pneumoniae*) is the primary agent of community-acquired pneumonia and to a high degree associated with bacteremia. The annual incidence of pneumonia is estimated from 1 to 12 per 1000 population in developed countries. Pneumococcal bacteremia ranges from 9 to 18 per 100,000 per year. Mortality of pneumococcal bacteremia ranges from 17% to 36% with highest mortality in the elderly.

The urokinase-type plasminogen activator receptor (uPAR/CD87) is expressed on different cell types including neutrophils, lymphocytes, macrophages, endothelial and malignant cells.

It is well known that uPAR is implicated in numerous biological functions. uPAR and its ligand urokinase-type plasminogen activator (uPA) are involved in converting plasminogen into plasmin. In addition, uPAR binds β integrins as well as signals the recruitment of inflammatory cells[10]. In the pathogenesis of cancer, uPA and uPAR play a key role in tissue invasion by the degradation of extracellular matrix. uPAR can be cleaved from the cell surface by a number of proteases, such as chymotrypsin, phospholipase C and uPA[19]. The proteolytic cleavage of uPAR from the cell surface releases a chemotactic active form of suPAR. Alternatively, uPAR is released/secreted from the cell surface without proteolysis.

Recently, we reported a strong correlation between advancing disease state of HIV-1 infection and elevated suPAR suggesting the use of suPAR as a prognostic marker. Finally, as shown in this patent application, patients with pulmonary tuberculosis have increased serum levels of suPAR.

The possible role of suPAR and uPA in immune responses towards other infectious diseases remains unclear. Gene knockout mice lacking uPAR have showed reduced pulmonary neutrophile recruitment and increased mortality to infection with *S. pneumoniae* compared to wildtype mice[20]. Lipotechoic acid from *Streptococcus pyogenes* facilitates monocyte uPAR upregulation in vitro. Upregulation of uPAR by monocytes induced by *Borrelia burgdorferi* surface proteins has also been reported[21].

The serum level of the protein YKL-40 has been described elevated during pneumonia and as an independent prognostic factor in pneumococcal bacteremic patients. Here we investigate whether *S. pneumoniae* bacteremia affects the plasma suPAR level. We report, for the first time, that suPAR is elevated and carries prognostic value in patients with *S. pneumoniae* bacteremia.

Subjects and Methods

Patients. Between October 1999 and June 2001, adults (18 years or older) with *S. pneumoniae* bacteremia admitted to one of five university hospitals (Aalborg, Aarhus, Odense, Hvidovre or Rigshospitalet) in Denmark were included. Blood samples were drawn at inclusion (hospital admission) and clinical data during the time of admission were collected prospectively, as described (G. Kronborg, N. Weis, H. O. Madsen, S. S. Pedersen, C. Wejse, H. Nielsen, P. Skinhøj, P. Garred, submitted for publication). Blood was drawn from a group of 30 healthy individuals (laboratory workers) for comparison (control group).

A total of 141 patients, 77 females and 64 males were included. The mean age of the patients was 64 years with a range of 20-99 years. Sixty-six percent of the patients had an underlying illness and pneumonia was the most common focus of infection (n=116). Twenty-four patients died in hospital (case-fatality rate =17%). Baseline characteristics of the patients are given in TABLE 3. All patients received appropriate antibiotic treatment from either admission or when the blood culture became positive. The study was approved by the local ethical committees.

ELISA. Maxisorb plates (Nunc, Roskilde, Denmark) were coated and incubated overnight at 4° C. with 100 µl 2 µg/ml murine monoclonal anti-suPAR antibody against human suPAR, diluted in coating buffer (15.1 mM $Na_2CO_3$, 35.7 mM $NaHC_3$, pH 9.6). Plates were washed with buffer (PBS, 0.1% Tween 20) and blocked using SuperBlock (Pierce Chemicals) diluted 1:1 in PBS. Plasma samples diluted in dilution buffer (7.3 mM $KH_2PO_4$, 50.7 mM $Na_2HPO_4$, 0.1 M NaCl, 0.5% phenol red, pH 7.4) were added and plates incubated overnight at 4° C. Bound suPAR was detected using 1001 µl 1.0 µg/ml rabbit anti-human suPAR polyclonal ab (a kind gift from dr. Gunilla Hoyer-Hansen) and mouse anti-rabbit polyclonal ab conjugated with alkaline phosphatase (Sigma, St. Louis, Mo., USA), diluted 1:2000. Each step preceded by 6 times washing with washing buffer, the antibodies were diluted in dilution buffer and plates incubated 1 h at 37° C. Substrate (1 tablet p-nitrophenyl phosphate (Sigma, St. Louis, Mo., USA) in 12 ml 0.1 Tris base, 0.1 M NaCl, 5 mM $MgCl_2$, pH 9.5) was added to the wells and incubated at room temperature for 30 min. Reactions were stopped by adding 50 µl 1 M NaOH per well and absorbance was read at 405 nm. All ELISA measurements were carried out in duplicates. YKL-40 was measured by ELISA.

Statistics. Comparisons between groups were made with Mann Whitney U test. suPAR as prognostic marker was analysed using logistic regression analysis. A p value below 0.05 was considered as significant. All analyses were carried out using SPSS software (SPSS, Chicago, Ill., USA).

Figure 5A:
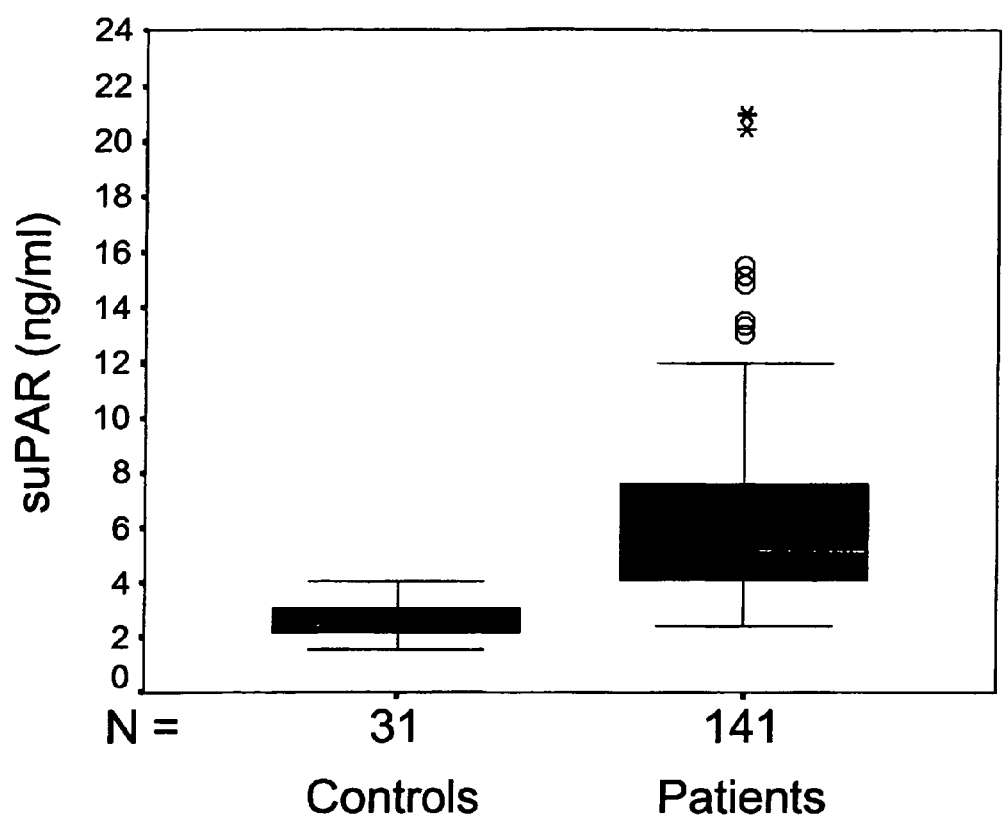
Figure 5B:
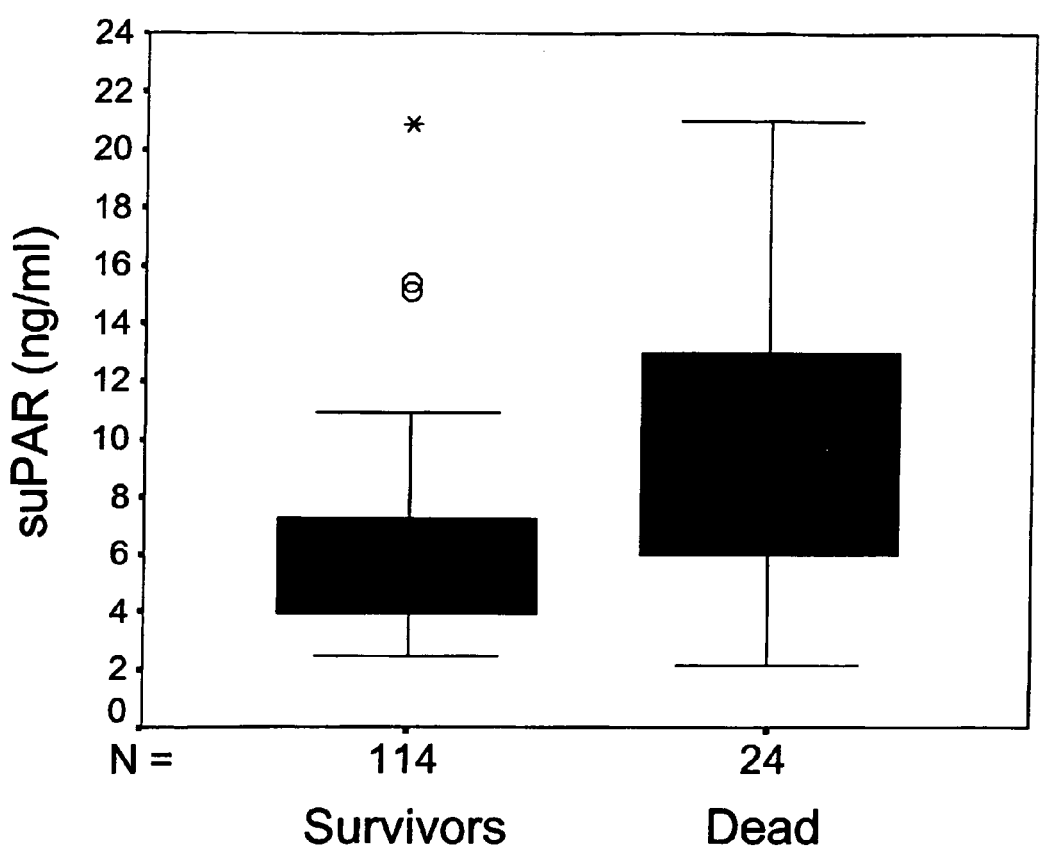

Results suPAR is elevated in pneumococcal bacteremic patients. The plasma level of suPAR was measurable in all the 141 samples with a median value of 5.5 ng/ml (range 2.4-21.0 ng/ml). The median level of suPAR in the control group was 2.6 ng/ml (range 1.54.0 ng/ml). The suPAR levels in the pneumococcal bacteremic patients were significantly higher than in the healthy controls (FIG. 5A, p=0.001).

suPAR predicts outcome of the infection. Division of the patients into one group surviving the infection (n=117) and one group of patients where the infection ended with death (n=24) showed significantly higher suPAR levels in the latter group (FIG. 5B; p=0.0001). Of the dead patients, 79% (n=19) had suPAR levels above the median of 5.5 ng/ml.

The clinical parameters of prognostic importance in terms of death due to the infection were, as described (G. Kronborg et al., submitted for publication): cerebral symptoms (confusion, unconsciousness) at time of admission (p=0.03), hypotension (p=0.047) and kidney failure (p=0.002); see TABLE 1. The suPAR level was significantly elevated in patients with hypotension (p=0.0001) and renal failure (p=0.0001). suPAR was also elevated in the group of chronic alcohol abusers (p=0.0001). Underlying diseases were not significantly associated to a deadly outcome of pneumococcal bacteremia, except for alcoholism (p=0.04).

suPAR is correlated to YKL-40, but not CRP. YKL-40 is a lectin secreted from neutrophils and macrophages (25). When comparing suPAR levels with the YKL-40 levels (n=89), we found a strong correlation between suPAR and YKL-40 (Spearman rank correlation coefficient: 0.70, p=0.0001).

Most of the patients had measured their level of CRP. There was no correlation between suPAR levels and CRP levels (n=131). High CRP levels were not prognostic of death.

suPAR is an independent prognostic marker. In a logistic multivariate regression analysis (TABLE 3) including all parameters found to be significant in univariate analysis (cerebral symptoms, mechanical ventilation, treatment of hypotension, renal failure, alcohol abuse and YKL-40) only suPAR remained significantly associated with death. Patients with plasma suPAR above 10 ng/ml had a mortality rate (MR) of 13 (p=0.04) and an increase of 1.31 per ng suPAR (95% CI: 1.10-1.57), suPAR ranged from 2.4 to 21 ng/ml.

Discussion

In this study, we demonstrate for the first time that suPAR levels are highly elevated in patients with pneumococcal bacteremia. Elevated suPAR levels have previously been detected in patients with various forms of malignant diseases as well as in HIV-1 infection and in related lung diseases e.g. patients with untreated active tuberculosis.

Plasma suPAR is a strong predictor of death with a mortality rate of 1.31 per ng suPAR increase (suPAR varied between 2.4 and 21.0 ng/ml) in pneumococcal bacteremia. From this study we can only draw conclusions about the prognostic value of suPAR to patients with pneumococcal bacteremia. Hypotension, kidney failure, cerebral symptoms, chronic alcohol abuse and elevated plasma YKL-40 were all of prognostic value, but only elevated suPAR levels was an independent predictor of death in multivariate logistic regression analysis. We suggest plasma suPAR as a novel prognostic marker for patients with pneumococcal infections.

It is difficult to compare the suPAR values from the different studies because of inter-assay variations as well as differences in the clinical conditions of the patients included. However, suPAR seems to be highly elevated in patients with pneumococcal bacteremia compared to healthy controls. In a study by Riisbro et al., 53 patients with ovarian cancer had a median suPAR level of 1.3 ng/ml and healthy subjects had a median level of 0.9 ng/ml giving a rise of 44% in the cancer patients. Pneumococcal patients had a markedly higher increase in median suPAR of 112% compared to healthy controls.

We found a close correlation between suPAR and YKL-40. In the multivariate analysis YKL-40 above 500 ng/ml, cerebral symptoms, and hemodialysis were associated with elevated MR, but they were not of significance.

Elevated plasma suPAR has been reported from a group (n=13) of ICU sepsis patients[22], leading to speculations that the secretion of suPAR is increased during acute inflammation. We compared suPAR levels to CRP and found no correlation. This finding is supported by Slot et al.[6] who found no correlation between suPAR and CRP in patients with rheumatic diseases. Thus, this study find substantial evidence to rule out the possibility of suPAR being an acute phase reactant.

Evidence of the origin of plasma suPAR remains scarce. However, it is known that uPAR consists of three domains and proteolytic cleavage between domain 1 (D1) and 2+3 (D2D3) renders the chemotactic active domain D2D3[10]. Proteolytic cleavage is mediated by both its own ligand, uPA, and by different proteases, e.g. chymotrypsin. We have used a catching antibody of monoclonal anti-uPAR directed against domain 3 in our ELISA. This means that both intact suPAR and the chemotactic domain D2D3 were detected in our assay. The elevated plasma suPAR seen in pneumococcal bacteremia may be caused by increased secretion from leukocytes. During pneumococcal pneumonia, cytokines and different chemotactants are released and increased mortality is associated with a high pulmonary interleukin-6 level.

uPAR plays an important role in both innate and acquired immunity. In transgenic mice lacking uPAR May[23] et al. showed the presence of uPAR to be crucial for leukocytes to adhere to the endothelium. Knockout mice lacking uPAR show a diminished immune response to S. pneumoniae with decreased neutrophile recruitment to the lung and mice lacking uPA had an increased immune response to *S. pneumoniae*[20]. These observations suggest that uPAR is needed for neutrophil recruitment but the mechanism is independent of proteolytic ability. In addition to plasmin activation, uPAR is believed to mediate cell-to-cell interaction through integrins and thereby involved in signal transduction. It is well described that invasive bacteria use the host plasmin system to degrade extracellular matrix, e.g. group A streptococci activate plasminogen by streptokinase. The possible proteolytic role of uPAR/uPA in neutrophil and monocyte migration against *Tuberculosis* and *Streptococcus pneumoniae* needs still to be investigated.

The reported elevations of plasma suPAR during bacteremia might reflect upregulation of uPAR on neutrophils, monocytes and vascular cells and indicate increased neutrophil and monocyte activity. In conclusion, similar to patients with tuberculosis, plasma suPAR is elevated and an independent predictor of death in patients with pneumococcal bacteremia.

TABLE 3

| Characteristic | | n | % | mortality (%) |
|---|---|---|---|---|
| Age, years | 18-60 | 54 | 39 | 11 |
| | 61-75 | 50 | 35 | 22 |
| | >75 | 37 | 26 | 19 |
| Male | | 64 | 45 | 21 |

| Univariate analysis | | n | MR | 95% CI | p |
|---|---|---|---|---|---|
| Treatment of hypotension# | | 19 | 3.0 | 1.0-9.0 | 0.05 |
| Cerebral symptoms# | | 41 | 2.9 | 1.1-7.4 | 0.03 |
| Hemodialysis# | | 11 | 8.4 | 2.3-30.7 | 0.002 |
| Alcoholism | | 21 | 3.0 | 1.0-8.5 | 0.04 |
| YKL-40 | 0-200 ng/ml | 29 | 1.0 | — | — |
| | 201-500 | 30 | 1.5 | 0.2-9.0 | 0.6 |
| | 501- | 30 | 11.8 | 2.4-58.8 | 0.003 |
| suPAR | 0-5 ng/ml | 64 | 1.0 | — | — |
| | 5.1-10 | 55 | 3.0 | 0.8-10.1 | 0.08 |
| | 10.1- | 19 | 20.6 | 5.3-80 | 0.0001 |

| Multivariate analysis | | n | MR | 95% CI | p |
|---|---|---|---|---|---|
| Treatment of hypotension# | | 19 | 0.1 | 0-2 | 0.1 |
| Cerebral symptoms# | | 41 | 3.7 | 0.8-17.1 | 0.09 |
| Hemodialysis# | | 11 | 6.4 | 0.3-118 | 0.2 |
| Alcoholism | | 21 | 0.8 | 0.2-6.2 | 0.8 |
| YKL-40 | 0-200 ng/ml | 29 | 1.0 | — | — |
| | 201-500 | 30 | 0.8 | 0.08-7.9 | 0.8 |
| | 501- | 30 | 3.9 | 0.4-35 | 0.2 |
| suPAR | 0-5 ng/ml | 64 | 1.0 | — | — |
| | 5.1-10 | 55 | 2.2 | 0.3-16.8 | 0.4 |
| | 10.1- | 19 | 13.0 | 1.1-158 | 0.04 |

Example 4

Correlation Between Smear Positivity for TB and suPAR Level

Aim:

To determine whether suPAR has diagnostic value in TB infection by comparing to microscopic analysis.

Material and Subjects 69 patients from four suburban areas in Bissau, the capital of Guinea Bissau was included in the study. Criterion for inclusion in the study was one or more of the following symptoms and signs without other explanatory disease: persistent cough (>1 month) without improvement on antibiotics, constant or periodic fever for more than 1 month, weight loss, dyspnoea, haemoptysis, nightly sweats or lymphadenopathy. suPAR was measured in sputum from 69 patients. All patients were tested for Acid Fast Bacilli (AFB) in sputum direct microscopy. SuPAR was measured using ELISA.

Results

All 69 individuals had measurable suPAR in sputum. Median suPAR was 24.9 ng/ml sputum (range 3.1-50.0). Nine patients were positive for AFB in direct microscopy, and these patients had a median suPAR of 50 ng/ml (max in assay, range 9,73-50). This was significantly higher than among 60 patients negative for AFP in direct microscopy (median suPAR 20.3 ng/ml; range 3.1-50 ng/ml), p=0.002 Mann Whitney test (FIG. 6).

Discussion

This study shows that patients positive for AFB have significantly higher suPAR levels than individuals negative for AFB in direct microscopy. Thus, suPAR carries diagnostic information on TB sputum positivity in TB patients.

Example 5

Patients with Active TB Have Higher suPAR in Sputum

Aim:

To determine whether suPAR is measurable in sputum and whether patients who receive therapy has lower suPAR levels than patients who are TB positive but do not receive therapy.

Materials and Subjects 25 patients from four suburban areas in Bissau, the capital of Guinea Bissau was included in the study. Criterion for inclusion in the study was one or more of the following symptoms and signs without other explanatory disease: persistent cough (>1 month) without improvement on antibiotics, constant or periodic fever for more than 1 month, weight loss, dyspnoea, haemoptysis, nightly sweats or lymphadenopathy. suPAR was measured in sputum from 25 patients. All patients had signs, symptoms and x-ray-changes compatible with active TB in the chest and with findings of Acid Fast Bacilli (AFB) in sputum direct microscopy. Seven of the patients received therapy at the time of sputum sampling and 18 patients received therapy after the sputum sample was taken. The treatment consisted of a 4 months intensive phase of daily Directly Observed Treatment with Ethambutol, Isoniazid, Rifampicin, and Pyrazinamide was followed by a 4 months continuation phase with Isoniazid and Ethambutol collected at the health centre twice per month by the patient. This treatment regimen was recommended for HIV-infected individuals by the national tuberculosis programme in Guinea-Bissau when the research project was initiated in 1996. For reasons of confidentiality and comparability HIV-infected and uninfected individuals received the same treatment. In addition, all patients were given Vitamin B complex and Multivitamins daily. Adherence to treatment was verified by pill count and an INH urine test at 2, 5 and 8 months of follow-up. Defaulting patients were visited by the nurse and encouraged to continue treatment. Specific HIV drugs or prophylactic treatment for HIV-related diseases were not available in Guinea-Bissau, which is one of the poorest countries of the world.

Results 18 patients positive for AFB and 7 patients positive for AFB but receiving treatment. There was significantly higher suPAR levels in sputum for the patients whom did not receive therapy compared to the 7 TB patients that received therapy (p=0.024) (FIG. 7).

Discussion

In this study, we find that suPAR is measurable in sputum. Most importantly, we show that TB patients not receiving therapy has significantly higher suPAR levels compared to TB patients after therapy has been initiated. Thus, initiation of therapy results in a decrease in sputum suPAR and sputum suPAR measurement may therefore be used to monitor TB treatment efficacy.

Example 6

Aim:

To determine whether suPAR is measurable in spinal fluid

Materials and Methods

Spinal fluid was obtained from 23 patients with pneumococcal disease and from 1 control. SuPAR was measured using ELISA.

Results.

SuPAR was measurable in spinal fluid from all 24 individuals included in the study. The median suPAR was 3.49 ng/ml spinal fluid. The control patient had a suPAR value of 0.69 ng/ml.

Discussion.

Here we show that suPAR is measurable in spinal fluid. Thus, the measurement of suPAR in spinal fluid may be used for diagnostic and prognostic purposes.

Example 7

The suPAR level, is not influenced by HCV infection or by Alpha-Interferon and Ribavirin Therapy.

Background.

We have shown that the suPAR (soluble urokinase receptor) level increases in patients with HIV, Tuberculosis or s. pneumococcal infection and that suPAR is an independent highly significant prognostic marker for these diseases. The aim of this study was to determine whether suPAR level is altered by HCV infection and treatment. If suPAR is modulated by HCV infection, this may influence on the prognostic value of suPAR in HIV, Tuberculosis or s. pneumococcal infected patients coinfected with HCV.

Subjects and Methods:

Forty-seven HCV positive patients were treated with alpha-interferon and ribavirin for 12 months. All patients were HIV and HBV negative. Blood samples were drawn immediately prior to therapy (T0), and the end of treatment (T12) and 6-month later (T18). Plasma samples from 30 healthy controls were included for comparisons. suPAR was measured using ELISA and HCV viral load by RT-PCR.

Results:

There was a significant drop in HCV viral load after therapy (paired samples t test, p=0.033). There was no difference in suPAR levels between patients before treatment (Median suPAR: 2.58 ng/ml (range 1.15-6.01), after treatment (median suPAR: 2.52 ng/ml (range 1.24-6.26) and at 6-month follow-up (median suPAR 2.43 ng/ml (range 1,21-4,98). No difference in suPAR was observed between patients and controls (p=0.68). suPAR was highly correlated at all time points (T0-T12, T0-T18, and T12-T18, all p<0.001, all r>0.67, Pearson correlation). In addition, there was no difference in suPAR between the 30 responders and 19 nonresponders (p=0.39).

Conclusion:

The plasma level of suPAR remained stable over time indicating the possible use of suPAR as a serological marker. The serum suPAR level is not influenced by HCV infection, HCV titer, by introduction of alpha-interferon and ribavirin therapy, or by response to therapy. These data suggests that HCV/HIV coinfection does not influence on suPAR as a prognostic marker in HIV infected, Tuberculosis or s. pneumococcal infected patients individuals.

Example 8

The expression of uPAR on PBMC correlates with serum level of suPAR.

Background.

To determine whether there is a significant relationship between surface expression of uPAR and serum level of suPAR.

Methods:

Blood was collected from 10 healthy blood donors attending the donor clinic at Hvidovre Hospital. The serum was collected and suPAR concentration measured using ELISA. PBMC was collected using Histopaq gradient centrifugation, and the expression of CD87 was measured using R2 antibody, and a secondary FITC conjugated antibody against mouse antibody using FACS analysis. An idiotypic negative control antibody was included as control of specificity.

Results:

All blood donors had measurable uPAR receptor on the PBMC and measurable suPAR in serum. The serum suPAR levels significantly correlated with the uPAR surface expression (Pearson correlation, p<0.05) (FIG. 8).

Discussion.

Here we have shown a significant relationship PBMC surface expression of uPAR (CD87) and the serum level of suPAR. This is in accordance with the observations of others[11] who also find that uPAR on circulating cells correlate significantly with the plasma/serum suPAR level. Thus, it is therefore reasonable to assume that the surface expression of uPAR may be a strong prognostic factor in patients with Streptococcus pneumoniae or Mycobacterium tuberculosis infection. The CD87 (uPAR) could be measured using FACS and thereby add valuable information regarding diagnosis as well as the patients progression status.

REFERENCE LIST

1. Nykjaer, A., B. Moller, R. F. Todd, III, T. Christensen, P. A. Andreasen, J. Gliemann, and C. M. Petersen. 1994. Urokinase receptor. An activation antigen in human T lymphocytes. *J Immunol* 152:505-516.
2. Speth, C., I. Pichler, G. Stockl, M. Mair, and M. P. Dierich. 1998. Urokinase plasminogen activator receptor (uPAR; CD87) expression on monocytic cells and T cells is modulated by HIV-1 infection. *Immunobiology* 199:152-162.
3. Sier, C. F., N. Sidenius, A. Mariani, G. Aletti, V. Agape, A. Ferrari, G. Casetta, R. W. Stephens, N. Brunner, and F. Blasi. 1999. Presence of urokinase-type plasminogen activator receptor in urine of cancer patients and its possible clinical relevance. *Lab Invest* 79:717-722.
4. Stephens, R. W., H. J. Nielsen, I. J. Christensen, O. Thorlacius-Ussing, S. Sorensen, K. Dano, and N. Brunner. 1999. Plasma urokinase receptor levels in patients with colorectal cancer: relationship to prognosis. *J. Natl. Cancer Inst.* 91:869-874.
5. Ninomiya, H., Y. Hasegawa, T. Nagasawa, and T. Abe. 1997. Excess soluble urokinase-type plasminogen activator receptor in the plasma of patients with paroxysmal nocturnal hemoglobinuria inhibits cell-associated fibrinolytic activity. *Int J Hematol.* 65:285-291.
6. Slot, O., N. Brunner, H. Locht, P. Oxholm, and R. W. Stephens. 1999. Soluble urokinase plasminogen activator receptor in plasma of patients with inflammatory rheumatic disorders: increased concentrations in rheumatoid arthritis. *Ann. Rheum. Dis.* 58:488-492.
7. Sidenius, N., C. F. Sier, H. Ullum, B. K. Pedersen, A. C. Lepri, F. Blasi, and J. Eugen-Olsen. 2000. Serum level of soluble urokinase-type plasminogen activator receptor is a strong and independent predictor of survival in human immunodeficiency virus infection. *Blood* 96:4091-4095.
8. Holst-Hansen, C., M. J. Hamers, B. E. Johannessen, N. Brunner, and R. W. Stephens. 1999. Soluble urokinase receptor released from human carcinoma cells: a plasma parameter for xenograft tumour studies. *Br. J. Cancer* 81:203-211.
9. Stephens, R. W., H. J. Nielsen, I. J. Christensen, O. Thorlacius-Ussing, S. Sorensen, K. Dano, and N. Brunner. 1999. Plasma urokinase receptor levels in patients with colorectal cancer: relationship to prognosis. *J. Natl. Cancer Inst.* 91:869-874.
10. Fazioli, F., M. Resnati, N. Sidenius, Y. Higashimoto, E. Appella, and F. Blasi. 1997. A urokinase-sensitive region of the human urokinase receptor is responsible for its chemotactic activity. *EMBO J.* 16:7279-7286.
11. Mustjoki, S., N. Sidenius, C. F. Sier, F. Blasi, E. Elonen, R. Alitalo, and A. Vaheri. 2000. Soluble urokinase receptor levels correlate with number of circulating tumor cells in acute myeloid leukemia and decrease rapidly during chemotherapy. *Cancer Res.* 60:7126-7132.
12. Fernebro, E., R. R. Madsen, M. Ferno, N. Brunner, P. Bendahl, I. J. Christensen, A. Johnson, and M. Nilbert. 2001. Prognostic importance of the soluble plasminogen activator receptor, suPAR, in plasma from rectal cancer patients. *Eur. J. Cancer* 37:486-491.
13. Lisse, I. M., H. Whittle, P. Aaby, M. Normark, A. Gyhrs, and L. P. Ryder. 1990. Labelling of T cell subsets under field conditions in tropical countries. Adaptation of the immuno-alkaline phosphatase staining method for blood smears. *J Immunol Methods* 129:49-53.
14. Ross, G. D. 2000. Regulation of the adhesion versus cytotoxic functions of the Mac-1/CR3/alphaMbeta2-integrin glycoprotein. *Crit Rev. Immunol.* 20:197-222.
15. Sier, C. F., R. Stephens, J. Bizik, A. Mariani, M. Bassan, N. Pedersen, L. Frigerio, A. Ferrari, K. Dano, N. Brunner, and F. Blasi. 1998. The level of urokinase-type plasminogen activator receptor is increased in serum of ovarian cancer patients. *Cancer Res.* 58:1843-1849.
16. Stephens, R. W., A. N. Pedersen, H. J. Nielsen, M. J. Hamers, G. Hoyer-Hansen, E. Ronne, E. Dybkjaer, K. Dano, and N. Brunner. 1997. ELISA determination of soluble urokinase receptor in blood from healthy donors and cancer patients. *Clin. Chem.* 43:1868-1876.
17. Juffermans, N. P., P. E. Dekkers, A. Verbon, P. Speelman, S. J. van Deventer, and P. T. van Der. 2001. Concurrent upregulation of urokinase plasminogen activator receptor and cd11b during tuberculosis and experimental endotoxemia. *Infect. Immun.* 69:5182-5185.
18. Melo, M. D., I. R. Catchpole, G. Haggar, and R. W. Stokes. 2000. Utilization of CD11b knockout mice to characterize the role of complement receptor 3 (CR3, CD11b/CD18) in the growth of *Mycobacterium tuberculosis* in macrophages. *Cell Immunol.* 205:13-23.
19. Hoyer-Hansen, G., E. Ronne, H. Solberg, N. Behrendt, M. Ploug, L. R. Lund, V. Ellis, and K. Dano. 1992. Urokinase plasminogen activator cleaves its cell surface receptor releasing the ligand-binding domain. *J Biol Chem* 267: 18224-18229.
20. Rijneveld, A. W., M. Levi, S. Florquin, P. Speelman, P. Carmeliet, and P. T. van Der. 2002. Urokinase receptor is necessary for adequate host defense against pneumococcal pneumonia. *J. Immunol.* 168:3507-3511.
21. Coleman, J. L., J. A. Gebbia, and J. L. Benach. 2001. *Borrelia burgdorferi* and other bacterial products induce expression and release of the urokinase receptor (CD87). *J. Immunol.* 166:473-480.
22. Mizukami, I. F., N. E. Faulkner, M. R. Gyetko, R. G. Sitrin, and R. F. Todd, III. 1995. Enzyme-linked immunoabsorbent assay detection of a soluble form of urokinase plasminogen activator receptor in vivo. *Blood* 86:203-211.
23. May, A. E., F. J. Neumann, A. Schomig, and K. T. Preissner. 2000. VLA4 (alpha(4)beta(1)) engagement defines a novel activation pathway for beta(2) integrin-dependent leukocyte adhesion involving the urokinase receptor. *Blood* 96:506-513.

The invention claimed is:
1. A method of evaluating the progression of the state of a subject suffering from pneumococcal bacteremia comprising (a) measuring in vitro the level of one or more markers selected from the group consisting of (i) urokinase plasminogen activator receptor (uPAR), (ii) soluble urokinase plasminogen activator receptor (suPAR), and (iii) one or more degradation products of (i) or (ii), in each of a number of biological fluid samples from the subject, wherein the samples are obtained at different points in time, (b) comparing the measured levels, wherein a decrease in the levels over time indicates an improvement of the state of the subject.
2. A method of evaluating the progression of the state of a subject suffering from a respiratory bacterial infection comprising a) measuring in vitro the level of one or more markers selected from the group consisting of (i) urokinase plasminogen activator receptor (uPAR), (ii) soluble urokinase plasminogen activator receptor (suPAR), and (iii) one or more degradation products of (i) or (ii), in each of a number of biological fluid samples from the subject, wherein the samples are obtained at different points in time, (b) comparing the measured levels, wherein a decrease in the levels over time indicates an improvement of the state of the subject.
3. A method according to claim 2, wherein the respiratory bacterial infection is a *Streptococcus pneumoniae* infection.
4. A method according to claim 2, wherein the respiratory bacterial infection is a *Mycobacterium tuberculosis* infection.
5. A method according to claim 2, wherein the subject is undergoing a treatment regimen.
6. A method according to claim 1, wherein the biological fluid sample is a urine sample.
7. A method according to claim 1, wherein the biological fluid sample is a serum or blood sample.
8. A method according to claim 1, wherein the measuring is done using a stick.
9. A method according to claim 1, wherein the measuring is done using ELISA.
10. The method of claim 1, wherein the marker is suPAR.
11. A method according to claim 2, wherein the biological fluid sample is a urine sample.
12. A method according to claim 2, wherein the biological fluid sample is a serum or blood sample.
13. A method according to claim 2, wherein the measuring is done using a stick.
14. A method according to claim 2, wherein the measuring is done using ELISA.
15. The method of claim 2, wherein the marker is suPAR.
16. The method of claim 1, further comprising the step of simultaneously confirming in vitro for infection by a pneu- mococcal bacteria, wherein a decrease in the levels over time in infected individuals indicates an improvement of the state of the subject.

17. The method of claim 2, further comprising the step of simultaneously confirming in vitro for infection by a respiratory bacterial pathogen, wherein a decrease in the levels over time in infected individuals indicates an improvement of the state of the subject.

* * * * *